United States Patent
Askew et al.

(10) Patent No.: US 8,901,144 B2
(45) Date of Patent: Dec. 2, 2014

(54) FLUORINATED 3-(2-OXO-3-(3-ARYLPROPYL) IMIDAZOLIDIN-1-YL)-3-ARYLPROPANOIC ACID DERIVATIVES

(71) Applicant: SciFluor Life Sciences, LLC, Cambridge, MA (US)

(72) Inventors: Ben C. Askew, Marshfield, MA (US); Richard W. Heidebrecht, Somerville, MA (US); Takeru Furuya, Cambridge, MA (US); Mark E. Duggan, Wellesley, MA (US)

(73) Assignee: SciFluor Life Sciences, LLC, Cambridge, MA (US)

( * ) Notice: Subject to any disclaimer, the term of this patent is extended or adjusted under 35 U.S.C. 154(b) by 0 days.

(21) Appl. No.: 14/175,501

(22) Filed: Feb. 7, 2014

(65) Prior Publication Data

US 2014/0221410 A1 Aug. 7, 2014

Related U.S. Application Data

(60) Provisional application No. 61/762,087, filed on Feb. 7, 2013.

(51) Int. Cl.
| | | |
|---|---|---|
| *A01N 43/54* | (2006.01) | |
| *A61K 31/505* | (2006.01) | |
| *C07D 471/04* | (2006.01) | |

(52) U.S. Cl.
CPC .................................. *C07D 471/04* (2013.01)
USPC ............ 514/274; 514/300; 544/296; 546/122

(58) Field of Classification Search
USPC .................... 544/296; 546/122; 514/274, 300
See application file for complete search history.

(56) References Cited

U.S. PATENT DOCUMENTS

| | | | |
|---|---|---|---|
| 5,501,969 A | 3/1996 | Hastings et al. | |
| 5,736,357 A | 4/1998 | Bromme et al. | |
| 6,017,926 A | 1/2000 | Askew et al. | |
| 6,211,184 B1* | 4/2001 | Duggan et al. | 514/255.02 |
| 6,268,378 B1* | 7/2001 | Duggan et al. | 514/300 |
| 6,291,503 B1 | 9/2001 | Schoop et al. | |
| 6,407,241 B1* | 6/2002 | Jensen et al. | 546/122 |
| 6,426,353 B1* | 7/2002 | Arison et al. | 514/300 |
| 6,472,403 B2* | 10/2002 | Duggan et al. | 514/300 |
| 2002/0016461 A1 | 2/2002 | Albers et al. | |
| 2004/0038963 A1 | 2/2004 | Wang | |
| 2004/0053968 A1* | 3/2004 | Hartman et al. | 514/333 |
| 2004/0249158 A1 | 12/2004 | Wells et al. | |
| 2005/0004199 A1* | 1/2005 | Hartman et al. | 514/406 |
| 2013/0129621 A1 | 5/2013 | Mackel et al. | |

FOREIGN PATENT DOCUMENTS

| | | |
|---|---|---|
| WO | WO 96/13523 A1 | 5/1996 |
| WO | WO 01/47867 A1 | 7/2001 |
| WO | WO 01/87840 A1 | 11/2001 |
| WO | WO 2011/150156 A2 | 12/2011 |
| WO | WO 2013/000909 A1 | 1/2013 |

OTHER PUBLICATIONS

R.S. Meissner et al., 12 Bioorganic & Medicinal Chemistry Letters, 25-29 (2002).*
Ali, Y. et al. "Industrial Perspective in Ocular Drug Delivery," Advanced Drug Delivery Reviews, 58:1258-1268 (2006).
Ando, M. et al., "Facile one-pot synthesis of N-difluoromethyl-2-pyridone derivatives" Organic Letters, 8(17):3805-3808 (2006).
Bourges, J.L. et al., "Ocular drug delivery targeting the retina and retinal pigment epithelium using polylactide nanoparticles," Invest. Ophthalmol. Vis. Sci. 44:3562-3569 (2003).
Bradshaw, B. et al., "Synthesis of 5-hydroxy-2,3,4,5-tetrahydro-[1H]-2-benzazepin-4-ones: selective antagonists of muscarinic ($M_3$) receptors," Org. Biomol. Chem., 6(12):2138-57 (2008).
Campochiaro, P.A., et al., "Reduction of Diabetic Macular Edema by Oral Administration of the Kinase Inhibitor PKC412," Invest. Ophthalmol. Vis. Sci., 45:922-931 (2004).
Cao, F., et al. "Zn—Al—NO3-layered double hydroxides with intercalated diclofenac for ocular delivery," International Journal of Pharmaceuticals, 404:250-256 (2011).
Chavakis, E. et al., "Kinetics of integrin expression in the mouse model of proliferative retinopathy and success of secondary intervention with cyclic RGD peptides," Diabetologia 45:262-267 (2002).
Coleman, P.J. et al. et al. "Nonpeptide $\alpha v \beta 3$ Antagonists. Part 11: Discovery and Preclinical Evaluation of potent $\alpha v \beta 3$ Antagonists for the Prevention and Treatment of Osteoporosis," J. Med. Chem., 47:4829-4837 (2004).
Diebold, Y. et al., "Applications of nanoparticles in ophthalmology," Progress in Retinal and Eye Research, 29:596-609 (2010).
Dorrell, M., "Combination angiostatic therapy completely inhibits ocular and tumor angiogenesis," Proceedings of the National Academy of Sciences of the United States of America, 104(3):967-972 (2007).
Doukas, J., et al., "Topical Administration of a Multi-Targeted Kinase Inhibitor Suppresses Choroidal Neovascularization and Retinal Edema," Journal of Cellular Physiology, 216:29-37 (2008).
Freund, K.B. et al., "Age-related Macular Degeneration and Choroidal Neovascularization," American Journal of Ophthalmology, 115:786-791 (1993).
Friedlander, P., Ber. Dtsch. Chem. Ges. 1882, 15, 2572-2575.
Friedlander, M. et al. "Involvement of integrins $\alpha_v\beta_3$ and $\alpha_v\beta_5$ in ocular neovascular diseases". *Proc Natl Acad Sci USA* 93:9764-9769 (1996).
Fu, Y., et al., "Angiogenesis Inhibition and Choroidal Neovascularization Suppression by Sustained Delivery of an Integrin Antagonist, EMD478761," Invest. Ophthalmol. Vis. Sci. 48(11):5184-5190 (2007).

(Continued)

*Primary Examiner* — James O Wilson
*Assistant Examiner* — Alexander R Pagano
(74) *Attorney, Agent, or Firm* — Cooley LLP

(57) ABSTRACT

The invention relates to fluorinated compounds and their use as integrin receptor antagonists. Novel fluorinated 3-(2-oxo-3-(3-arylpropyl)imidazolidin-1-yl)-3-arylpropanoic acid derivatives and pharmaceutically acceptable salts or solvates thereof and their use are described.

14 Claims, No Drawings

(56) References Cited

OTHER PUBLICATIONS

Gaudana, R. et al., "Recent perspectives in ocular drug delivery," Pharm Res., 26(5):1197-1216 (2009).
Hallinan, E.A. et al., "N-Substituted dibenzoxazepine as analgesic PGE$_2$ antagonists," J. Med. Chem., 36:3293-3299 (1993).
Jacot, J.L. et al., "Potential Therapeutic Roles for Inhibition of the PI3K/Akt/mTOR Pathway in the Pathophysiology of Diabetic Retinopathy," Journal of Ophthalmology, vol. 2011, Article ID 589813 (2011).
Kamizuru, H.K.H. et al., "Monoclonal antibody-mediated drug targeting to choroidal neovascularization in the Rat.," Investigative Opthalmology & Visual Science, 42:2664-2672 (2001).
Kaur, H., et al., "Niosomes: A Novel Drug Delivery System," Int J Pharm Sci Rev Res 15(1):113-120 (2012).
Kern, T.S., et al., "Topical administration of nepafenac inhibits diabetes-induced retinal microvascular disease and underlying abnormalities of retinal metabolism and physiology," *Diabetes.* 56(2):373-379 (2007).
Klein, R. et al., "The Wisconsin Epidemiologic Study of diabetic retinopathy. XIV. Ten-year incidence and progression of diabetic retinopathy," Arch Ophthalmol, 112:1217-1228 (1994).
Linderman, R.J., "Oxidation of Fluoroalkyl-Substituted Carbinols by the Dess-Martin Reagent," J. Org. Chem., 54(3):661-668 (1989).
Luna, J. et al. "Antagonists of Integrin αvβ3 Inhibit Retinal Neovascularization in a Murine Model," Laboratory Investigation, 75(4):563-573 (1996).
Millauer, B., et al., "Dominant-Negative Inhibition of Flk-1 Suppresses the Growth of Many Tumor Types in Vivo", Cancer Research 56:1615-1620 (1996).
Murphy, M.G., et al., "Effect of L-000845704, an $α_vβ_3$ Integrin Antagonist, on Markers of Bone Turnover and Bone Mineral Density in Postmenopausal Osteoporotic Women," The Journal of Clinical Endocrinology & Metabolism, 90(4):2022-2028 (2005).
Nahm, S., et al., "N-methoxy-n-methyl amides as effective acylating agents," Tetrahedron Letters, 22(39):3815-3818 (1981).
Hutchison, John H., et al., Nonpeptide $α_vβ_3$ Antagonists. 8. In Vitro and In Vivo Evaluation of a Potent $α_vβ_3$ Antagonist for the Prevention and Treatment of Osteoporosis, J. Med. Chem. 2003, 46, 4790-4798.
Pialat, A. et al., "Oxidative para-Triflation of Acetanilides" Organic Letters, 15:1764-1767 (2013).
Riecke, B. et al. "Topical Application of Integrin Antagonists Inhibit Proliferative Retinopathy" Horm Metab Res, 33:307-311 (2001).
Rabinow, Barrett E., "Nanosuspensions in Drug delivery" Nature Reviews Drug Discovery 3, 785-796 (2004).
Rowe, Raymond C., "Handbook of Pharmaceutical Excipients", Fifth Edition, Pharmaceutical Press and American Pharmacists Association (2006).
Santulli, R. et al., "Studies with an Orally Bioavailable αv Integrin Antagonist in Animal Models of Ocular Vasculopathy: Retinal Neovascularization in Mice and Retinal Vascular Permeability in Diabetic Rats," The Journal of Pharmacology and Experimental Therapeutics, 324:894-901 (2008).
Sato, I. et al., "Enantioselective Synthesis of Substituted 3-Quinolyl Alkanols and Their Application to Asymmetric Autocatalysis," Synthesis, 9:1419-1428 (2004).
Seebach, D. et al., "Total Synthesis of Myxovirescin, 1 Strategy and Construction of the Southeastern Part [O(1)—C(14)]", Liebigs Ann. Chem., 1994, pp. 701-717.
Sondej, S.C. et al., "Gem-Difluoro Compounds: A Convenient Preparation from Ketones and Aldehydes by Halogen Fluoride Treatment of 1,3-dithiolanes," J. Org. Chem., 51:3508-3513 (1986).
Speicher, M.A. et al. "Pharmacologic therapy for diabetic retinopathy," Expert Opin Emerging Drugs 8(1):239-250 (2003).
Stragies, R. et al. "Design and Synthesis of a New Class of Selective Integrin α5β1 antagonists" J. Med. Chem. 50:3786-3794 (2007).
Takagi, H. et al., "Role of Vitronectin Receptor-Type Integrins and Osteopontin in Ischemia-Induced Retinal Neovascularization," Japanese Opthalmological Society 46:270-278 (2002).
Takahashi, K et al. "Suppression and Regression of Choroidal Neovascularization by the Multitargeted Kinase Inhibitor Pazopanib," Arch. Ophthalmol., 127(4): 494-499 (2009).
Vandamme, Th.F., "Microemulsions as ocular drug delivery systems: recent developments and future challenges," Progress in Retinal and Eye Research, 21:15-34 (2002).
Wagh, V.D. et al. "Niosomes as ophthalmic drug delivery systems: a review." Journal of Pharmacy Research, 3(7):1558-1563 (2010).
Wang, W. et al. "The Antiangiogenic Effects of Integrin α5β1 Inhibitor (ATN-161) In Vitro and In Vivo," Invest. Ophthalmol. Vis. Sci., 52(10):7213-7220 (2011), Published online before print Aug. 3, 2011.
Williams, R. et al. "Epidemiology of diabetic retinopathy and madular oedema: a review," Eye, 18:963-983 (2004).
Yang, X.M., "Role of PI3K/Akt and MEK/ERK in Mediating Hypoxia-Induced Expression of HIF-1α and VEGF in Laser-Induced Rat Choroidal Neovascularization," Investigative Ophthalmology & Visual Science, 50(4):1873-1879 (2009).
Yanni, S.E. et al., "The effects of nepafenac and amfenac on retinal angiogenesis," Elsevier, Brain Research Bulletin, 81:310-319 (2010).
Yasuda, N., et al., "An Efficient Synthesis of an αvβ3 Antagonist," J. Org. Chem., 69:1959-1966 (2004).
Yasukawa, T, et al. "Inhibition of experimental choroidal neovascularization in rats by an $α_v$-integrin antagonist," Current Eye Research, 28(5):359-366 (2004).
Zarbin, M.A. "Current Concepts in the Pathogenesis of Age-Related Macular Degeneration" Arch. Ophthalmol. 122:598-614 (2004).
Zhou, Hong-Yan et al., "Nanoparticles in the ocular drug delivery," Int. J. Ophthalmol, 6(3):390-396 (2013).

* cited by examiner

FLUORINATED 3-(2-OXO-3-(3-ARYLPROPYL) IMIDAZOLIDIN-1-YL)-3-ARYLPROPANOIC ACID DERIVATIVES

CROSS-REFERENCE TO RELATED APPLICATION

This application claims priority to and the benefit of U.S. Ser. No. 61/762,087, filed on Feb. 7, 2013, the content of which is incorporated herein by reference in its entirety.

BACKGROUND

It is believed that a wide variety of disease states and conditions can be mediated by acting on integrin receptors and that integrin receptor antagonists represent a useful class of drugs. Integrin receptors are heterodimeric transmembrane proteins through which cells attach and communicate with extracellular matrices and other cells. Antagonists of the integrin receptors $\alpha v\beta 3$, $\alpha v\beta 5$, and/or $\alpha v\beta 6$ are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

SUMMARY OF THE INVENTION

The invention relates to novel fluorinated 3-(2-oxo-3-(3-arylpropyl)imidazolidin-1-yl)-3-arylpropanoic acid derivatives and their use as integrin receptor antagonists. These compounds or pharmaceutically acceptable salts or solvates thereof are useful for example in inhibiting bone resorption, treating or preventing osteoporosis, or inhibiting vascular restenosis, diabetic retinopathy, macular degeneration, angiogenesis, atherosclerosis, inflammation, wound healing, viral disease, tumor growth, or metastasis.

The invention provides a compound of formula I:

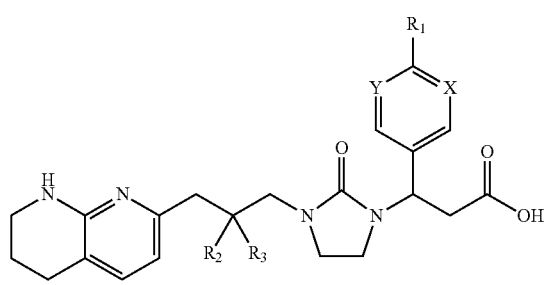

(I)

or a pharmaceutically acceptable salt or solvate thereof, wherein X, Y, $R_1$, $R_2$ and $R_3$ are as described herein and provided that the compound of formula I contains at least one fluorine atom.

The invention relates to pharmaceutical compositions comprising one of the compounds of the invention as an active ingredient. In one aspect, the invention provides a pharmaceutical composition comprising at least one compound of formula I, II, III, IV, or V or a pharmaceutically acceptable salt or solvate thereof and one or more pharmaceutically acceptable carriers, diluents, or excipients.

The invention relates to pharmaceutical compositions. The invention provides a pharmaceutical composition comprising a compound of the invention or a pharmaceutically acceptable salt or solvate thereof and one or more pharmaceutically acceptable carriers, diluents, or excipients, and which further comprises an active ingredient selected from the group consisting of a) an organic bisphosphonate or a pharmaceutically acceptable salt or ester thereof, b) an estrogen receptor modulator, c) a cytotoxic/antiproliferative agent, d) a matrix metalloproteinase inhibitor, e) an inhibitor of epidermal-derived, fibroblast-derived, or platelet-derived growth factors, f) an inhibitor of VEGF, g) an inhibitor of Flk-1/KDR, Flt-1, Tck/Tie-2, or Tic-1, h) a cathepsin K inhibitor, and i) a prenylation inhibitor, such as a farnesyl transferase inhibitor or a geranylgeranyl transferase inhibitor or a dual farnesyl/geranylgeranyl transferase inhibitor; and mixtures thereof.

The invention provides a pharmaceutical composition comprising a compound of the invention or a pharmaceutically acceptable salt or solvate thereof and one or more pharmaceutically acceptable carriers, diluents, or excipients, and which further comprises an active ingredient selected from the group consisting of a) an organic bisphosphonate or a pharmaceutically acceptable salt or ester thereof b) an estrogen receptor modulator, and c) a cathepsin K inhibitor; and mixtures thereof. In one aspect, the organic bisphosphonate or pharmaceutically acceptable salt or ester thereof is alendronate monosodium trihydrate.

The invention provides a pharmaceutical composition comprising a compound of the invention or a pharmaceutically acceptable salt or solvate thereof and one or more pharmaceutically acceptable carriers, diluents, or excipients, and which further comprises an active ingredient selected from the group consisting of a) a cytotoxic/antiproliferative agent, b) a matrix metalloproteinase inhibitor, c) an inhibitor of epidermal-derived, fibroblast-derived, or platelet-derived growth factors, d) an inhibitor of VEGF, and e) an inhibitor of Flk-1/KDR, Flt-1, Tck/Tie-2, or Tie-1; and mixtures thereof.

The invention relates to a method of eliciting an integrin receptor antagonizing effect in a subject in need thereof, comprising administering to the subject a therapeutically effective amount of a compound of the invention or a pharmaceutically acceptable salt or solvate, thereof. In one aspect, the integrin receptor antagonizing effect is an $\alpha v\beta 3$ antagonizing effect. In one aspect, the $\alpha v\beta 3$ antagonizing effect is selected from the group consisting of inhibition of bone resorption, restenosis, angiogenesis, diabetic retinopathy, macular degeneration, inflammation, viral disease, tumor growth, and metastasis. In one aspect, the $\alpha v\beta 3$ antagonizing effect is the inhibition of bone resorption.

In one aspect, the integrin receptor antagonizing effect is an $\alpha v\beta 5$ antagonizing effect. In one aspect, the $\alpha v\beta 5$ antagonizing effect is selected from the group consisting of inhibition of restenosis, angiogenesis, diabetic retinopathy, macular degeneration, inflammation, tumor growth, and metastasis.

In one aspect, the integrin receptor antagonizing effect is a dual $\alpha v\beta 3/\alpha v\beta 5$ antagonizing effect. In one aspect, the dual $\alpha v\beta 3/\alpha v\beta 5$ antagonizing effect is selected from the group consisting of inhibition of bone resorption, restenosis, angiogenesis, diabetic retinopathy, macular degeneration, inflammation, viral disease, tumor growth, and metastasis.

In one aspect, the integrin antagonizing effect is an $\alpha v\beta 6$ antagonizing effect. In one aspect, the $\alpha v\beta 6$ antagonizing effect is selected from the group consisting of angiogenesis, inflammatory response, and wound healing.

The invention relates to a method of eliciting an integrin receptor antagonizing effect in a subject in need thereof, comprising administering to the subject a therapeutically effective amount of a pharmaceutical composition comprising a compound of the invention or a pharmaceutically acceptable salt or solvate thereof and one or more pharmaceutically acceptable carriers, diluents, or excipients.

The invention relates to methods for the use of compounds of the invention. The compounds of the invention have a useful pharmacological activity spectrum and are therefore particularly suitable for the prevention and/or treatment of a condition.

The invention provides a method of treating and/or preventing a condition in a subject comprising administering to the subject in need thereof an effective amount of a compound of the invention or a pharmaceutically acceptable salt or solvate thereof. In one aspect, the invention provides treating a condition. In one aspect, the invention provides preventing a condition.

The invention provides a method of treating and/or preventing a condition in a subject comprising administering to the subject in need thereof an effective amount of a compound of the invention or a pharmaceutically acceptable salt or solvate, thereof, wherein the condition is mediated by antagonism of an integrin receptor. In one aspect, the invention provides treating a condition mediated by antagonism of an integrin receptor. In one aspect, the invention provides preventing a condition mediated by antagonism of an integrin receptor.

The invention provides a method of inhibiting bone resorption in a subject in need thereof, comprising administering to the subject a therapeutically effective amount of a pharmaceutical composition comprising a compound of the invention or a pharmaceutically acceptable salt or solvate thereof and one or more pharmaceutically acceptable carriers, diluents, or excipients.

The invention provides a method of inhibiting bone resorption in a subject in need thereof, comprising administering to the subject a therapeutically effective amount of a pharmaceutical composition comprising a compound of the invention or a pharmaceutically acceptable salt or solvate thereof and one or more pharmaceutically acceptable carriers, diluents, or excipients, and which further comprises an active ingredient selected from the group consisting of a) an organic bisphosphonate or a pharmaceutically acceptable salt or ester thereof, b) an estrogen receptor modulator, and c) a cathepsin K inhibitor; and mixtures thereof.

The invention provides a method of treating tumor growth in a subject in need thereof, comprising administering to the subject a therapeutically effective amount of a pharmaceutical composition comprising a compound of the invention or a pharmaceutically acceptable salt or solvate thereof and one or more pharmaceutically acceptable carriers, diluents, or excipients, and which further comprises an active ingredient selected from the group consisting of a) a cytotoxic/antiproliferative agent, b) a matrix metalloproteinase inhibitor, c) an inhibitor of epidermal-derived, fibroblast-derived, or platelet-derived growth factors, d) an inhibitor of VEGF, and e) an inhibitor of Flk-1/KDR, Flt-1, Tck/Tie-2, or Tie-1; and mixtures thereof.

The invention provides a method of treating a condition in a subject comprising administering to the subject in need thereof an effective amount of a compound of the invention or a pharmaceutically acceptable salt or solvate, thereof, in combination with radiation therapy wherein the condition is tumor growth.

DETAILED DESCRIPTION OF THE INVENTION

For purposes of the invention, the following definitions will be used (unless expressly stated otherwise):

"A compound of the invention" or "compounds of the invention" refers to a compound(s) disclosed herein e.g., a compound(s) of the invention includes a compound(s) of any of the formulae described herein including formula I, II, III, IV, or V and/or a compound(s) explicitly disclosed herein. Whenever the term is used in the context of the invention it is to be understood that the reference is being made to the free base and the corresponding pharmaceutically acceptable salts or solvates thereof, provided that such is possible and/or appropriate under the circumstances.

"Pharmaceutical" or "pharmaceutically acceptable" when used herein as an adjective, means substantially non-toxic and substantially non-deleterious to the recipient.

By "pharmaceutical composition" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

Some of the compounds of the invention may exist in unsolvated as well as solvated forms such as, for example, hydrates.

"Solvate" means a solvent addition form that contains either a stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the invention The invention also includes one or more metabolites of a compound of the invention.

For use in medicine, the salts of the compounds of the invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of the invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts which may be derived from ammonia or organic amines, such as, for example, diethylamine, triethylamine, ethyldiisopropylamine, procaine, dibenzylamine, N-methylmorpholine, dihydroabietylamine or methylpiperidine.

The invention includes within its scope prodrugs of the compounds of the invention. In general, such prodrugs will be functional derivatives of the compounds of the invention which are readily convertible in vivo into the required compound. Thus, in the methods of treatment of the invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of the invention into the biological milieu.

"Therapeutically effective amount" refers to that amount of a drug or pharmaceutical agent that will elicit the biological or medical response of a tissue, system, animal or human that is being sought by a researcher or clinician.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of the invention. The invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diasteriomeric mixture is often a mixture of diasteriomeric salts which is formed by contacting a racemic mixture of compounds with an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

"Treat," "treating," or "treatment" refers to decreasing the symptoms, markers, and/or any negative effects of a condition in any appreciable degree in a subject who currently has the condition. In some embodiments, treatment may be administered to a subject who exhibits only early signs of the condition for the purpose of decreasing the risk of developing the disease, disorder, and/or condition.

"Prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

"Subject" means a human or animal (in the case of an animal, more typically a mammal). In one aspect, the subject is a human.

"Fluorinated derivative" is a derivative compound that has the same chemical structure as the original compound, except that at least one atom is replaced with a fluorine atom or with a group of atoms containing at least one fluorine atom.

"Integrin receptor antagonist" refers to a compound which binds to and antagonizes either the $\alpha v\beta 3$ receptor, the $\alpha v\beta 5$ receptor, or the $\alpha v\beta 6$ receptor, or a compound which binds to and antagonizes combinations of these receptors (for example, a dual $\alpha v\beta 3/\alpha v\beta 5$ receptor antagonist).

"Bone resorption" refers to the process by which osteoclasts degrade bone.

"Alkoxy" refers to straight or branched chain alkoxides of the number of carbon atoms specified (e.g., $C_1$-$C_6$ alkoxy), or any number within this range (i.e., methoxy, ethoxy, etc.).

The problem to be solved by the invention is the identification of novel compounds which are antagonists of the integrin receptors $\alpha v\beta 3$, $\alpha v\beta 5$, and/or $\alpha v\beta 6$ and are useful for inhibiting bone resorption, treating or preventing osteoporosis, or inhibiting vascular restenosis, diabetic retinopathy, macular degeneration, angiogenesis, atherosclerosis, inflammation, wound healing, viral disease, tumor growth, or metastasis. Although integrin-targeted drugs are available, these drugs are often not suitable for patients for a variety of reasons. For example, the available antibody based therapies are often associated with a high cost of production, have an inconvenient mode of administration, and have a propensity for host immunogenicity and infusion reactions, and the available peptide-based drugs may lack specificity and require injections or intravenous administration, have high production costs, and limited stability. Small molecules represent another class of integrin-targeted drugs, however the compounds currently in the clinic and underdevelopment tend to be zwitterionic in nature and generally encounter limitations in bioavailability, serum protein binding, and integrin selectivity. Many integrin receptor antagonists are associated with undesired adverse effects. The invention provides the solution of new fluorinated integrin receptor antagonists useful for example in inhibiting bone resorption, treating or preventing osteoporosis, or inhibiting vascular restenosis, diabetic retinopathy, macular degeneration, angiogenesis, atherosclerosis, inflammation, wound healing, viral disease, tumor growth, or metastasis. The fluorinated compounds of the invention have advantages such as providing improved potency, selectivity, tissue penetration, half-life, and/or metabolic stability.

Compounds of the Invention

The present invention relates to novel fluorinated 3-(2-oxo-3-(3-arylpropyl)imidazolidin-1-yl)-3-arylpropanoic acid derivatives and their use.

In one aspect, the invention provides a compound of formula I:

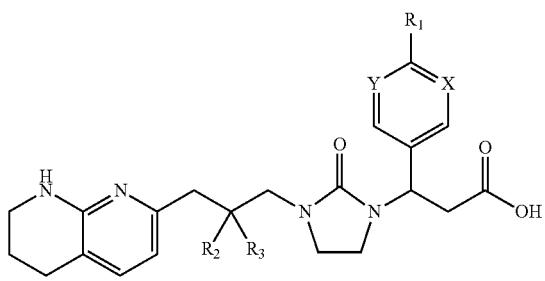

or a pharmaceutically acceptable salt or solvate thereof, wherein

X is selected from CH and N;
Y is selected from CH and N;
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula I contains at least one fluorine atom.

In one aspect, the invention provides a compound of formula II:

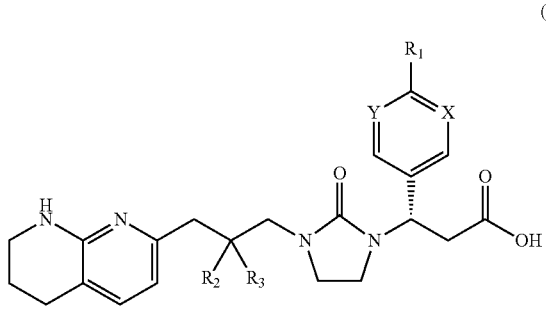

or a pharmaceutically acceptable salt or solvate thereof, wherein

X is selected from CH and N;
Y is selected from CH and N;
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula II contains at least one fluorine atom.

In one aspect, the invention provides a compound of formula I or II, wherein X is CH. In one aspect, the invention provides a compound of formula I or II, wherein X is N. In one aspect, the invention provides a compound of formula I or II, wherein Y is CH. In one aspect, the invention provides a compound of formula I or II, wherein Y is N. In one aspect, the invention provides a compound of formula I or II, wherein X or Y is CH and the remaining X or Y is N. In one aspect, the invention provides a compound of formula I or II, wherein X is N and Y is CH. In one aspect, the invention provides a compound of formula I or II, wherein X is CH and Y is N. In one aspect, the invention provides a compound of formula I or II, wherein X and Y are both CH. In one aspect, the invention provides a compound of formula I or II, wherein X and Y are both N.

In one aspect, the invention provides a compound of formula I or II, wherein $R_1$ is $C_1$-$C_6$ alkoxy substituted with 1, 2, 3, 4, or 5 fluorine atoms. In one aspect, the invention provides a compound of formula I or II, wherein $R_1$ is $C_1$-$C_6$ alkoxy substituted with 2 or 3 fluorine atoms. In one aspect, the invention provides a compound of formula I or II, wherein $R_1$ is selected from $OCH_3$, $OCH_2F$, $OCHF_2$, $OCF_3$, and $OCH_2CH_3$. In one aspect, the invention provides a compound of formula I or II, wherein $R_1$ is selected from $OCH_2F$, $OCHF_2$, and $OCF_3$. In one aspect, the invention provides a compound of formula I or II, wherein $R_1$ is selected from $OCH_3$ and $OCH_2CH_3$. In one aspect, the invention provides a compound of formula I or II, wherein $R_1$ is selected from $OCH_3$ and $OCHF_2$. In one aspect, the invention provides a compound of formula I or II, wherein $R_1$ is $OCH_3$. In one aspect, the invention provides a compound of formula I or II, wherein $R_1$ is $OCHF_2$.

In one aspect, the invention provides a compound of formula I or II, wherein $R_2$ is H. In one aspect, the invention provides a compound of formula I or II, wherein $R_2$ is F. In one aspect, the invention provides a compound of formula I or II, wherein $R_3$ is H. In one aspect, the invention provides a compound of formula I or II, wherein $R_3$ is F. In one aspect, the invention provides a compound of formula I or II, wherein one of $R_2$ or $R_3$ is H, and the remaining $R_2$ or $R_3$ is F. In one aspect, the invention provides a compound of formula I or II, wherein $R_2$ is H and $R_3$ is F. In one aspect, the invention provides a compound of formula I or II, wherein $R_2$ is F and $R_3$ is H. In one aspect, the invention provides a compound of formula I or II, wherein $R_2$ and $R_3$ are both H. In one aspect, the invention provides a compound of formula I or II, wherein $R_2$ and $R_3$ are both F. In one aspect, the invention provides a compound of formula I or II, wherein $R_2$ and $R_3$ taken together with the carbon atom to which they are attached form a 4-membered heterocyclic ring. In one aspect, the invention provides a compound of formula I or II, wherein the 4-membered heterocyclic ring is an oxetane ring. In one aspect, the invention provides a compound of formula I or II, wherein the oxetane ring is an oxetan-3-yl ring. In one aspect, the invention provides a compound of formula I or II, wherein the oxetane ring is an oxetan-2-yl ring.

In one aspect, the invention provides a compound of formula III:

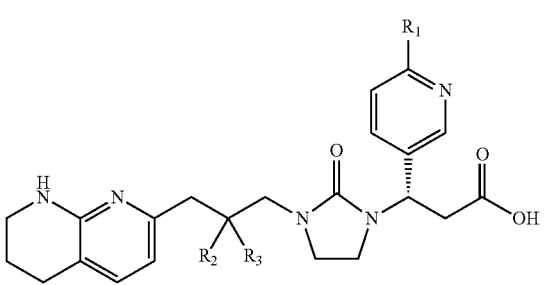

or a pharmaceutically acceptable salt or solvate thereof, wherein

R$_1$ is C$_1$-C$_6$ alkoxy wherein said C$_1$-C$_6$ alkoxy is substituted with 0, 1, 2, 3, 4, or 5 fluorine atoms; and R$_2$ and R$_3$ are each independently selected from H and F, or R$_2$ and R$_3$ taken together with the carbon atom to which they are attached form a 3- or 4-membered carbocyclic or heterocyclic ring, provided that the compound of formula III contains at least one fluorine atom.

In one aspect, the invention provides a compound of formula III, wherein R$_1$ is C$_1$-C$_6$ alkoxy substituted with 1, 2, 3, 4, or 5 fluorine atoms. In one aspect, the invention provides a compound of formula III, wherein R$_1$ is C$_1$-C$_6$ alkoxy substituted with 2 or 3 fluorine atoms. In one aspect, the invention provides a compound of formula III, wherein R$_1$ is selected from OCH$_3$, OCH$_2$F, OCHF$_2$, OCF$_3$, and OCH$_2$CH$_3$. In one aspect, the invention provides a compound of formula III, wherein R$_1$ is selected from OCH$_2$F, OCHF$_2$, and OCF$_3$. In one aspect, the invention provides a compound of formula III, wherein R$_1$ is selected from OCH$_3$ and OCH$_2$CH$_3$. In one aspect, the invention provides a compound of formula III, wherein R$_1$ is selected from OCH$_3$ and OCHF$_2$. In one aspect, the invention provides a compound of formula III, wherein R$_1$ is OCH$_3$. In one aspect, the invention provides a compound of formula III, wherein R$_1$ is OCHF$_2$.

In one aspect, the invention provides a compound of formula III, wherein R$_2$ is H. In one aspect, the invention provides a compound of formula III, wherein R$_2$ is F. In one aspect, the invention provides a compound of formula III, wherein R$_3$ is H. In one aspect, the invention provides a compound of formula III, wherein R$_3$ is F. In one aspect, the invention provides a compound of formula III, wherein one of R$_2$ or R$_3$ is H, and the remaining R$_2$ or R$_3$ is F. In one aspect, the invention provides a compound of formula III, wherein R$_2$ is H and R$_3$ is F. In one aspect, the invention provides a compound of formula III, wherein R$_2$ is F and R$_3$ is H. In one aspect, the invention provides a compound of formula III, wherein R$_2$ and R$_3$ are both H. In one aspect, the invention provides a compound of formula III, wherein R$_2$ and R$_3$ are both F. In one aspect, the invention provides a compound of formula III, wherein R$_2$ and R$_3$ taken together with the carbon atom to which they are attached form a 4-membered heterocyclic ring. In one aspect, the invention provides a compound of formula III, wherein the 4-membered heterocyclic ring is an oxetane ring. In one aspect, the invention provides a compound of formula III, wherein the oxetane ring is an oxetan-3-yl ring. In one aspect, the invention provides a compound of formula III, wherein the oxetane ring is an oxetan-2-yl ring.

In one aspect, the invention provides a compound of formula IV:

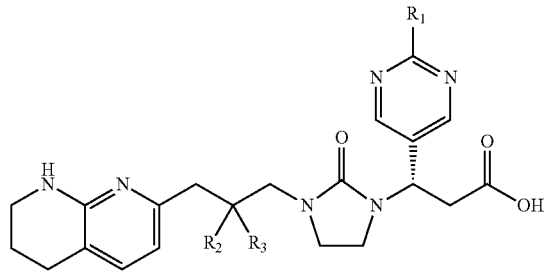

(IV)

or a pharmaceutically acceptable salt or solvate thereof, wherein

R$_1$ is C$_1$-C$_6$ alkoxy wherein said C$_1$-C$_6$ alkoxy is substituted with 0, 1, 2, 3, 4, or 5 fluorine atoms; and R$_2$ and R$_3$ are each independently selected from H and F, or R$_2$ and R$_3$ taken together with the carbon atom to which they are attached form a 3- or 4-membered carbocyclic or heterocyclic ring, provided that the compound of formula IV contains at least one fluorine atom.

In one aspect, the invention provides a compound of formula IV, wherein R$_1$ is C$_1$-C$_6$ alkoxy substituted with 1, 2, 3, 4, or 5 fluorine atoms. In one aspect, the invention provides a compound of formula IV, wherein R$_1$ is C$_1$-C$_6$ alkoxy substituted with 2 or 3 fluorine atoms. In one aspect, the invention provides a compound of formula IV, wherein R$_1$ is selected from OCH$_3$, OCH$_2$F, OCHF$_2$, OCF$_3$, and OCH$_2$CH$_3$. In one aspect, the invention provides a compound of formula IV, wherein R$_1$ is selected from OCH$_2$F, OCHF$_2$, and OCF$_3$. In one aspect, the invention provides a compound of formula IV, wherein R$_1$ is selected from OCH$_3$ and OCH$_2$CH$_3$. In one aspect, the invention provides a compound of formula IV, wherein R$_1$ is selected from OCH$_3$ and OCHF$_2$. In one aspect, the invention provides a compound of formula IV, wherein R$_1$ is OCH$_3$. In one aspect, the invention provides a compound of formula IV, wherein R$_1$ is OCHF$_2$.

In one aspect, the invention provides a compound of formula IV, wherein R$_2$ is H. In one aspect, the invention provides a compound of formula IV, wherein R$_2$ is F. In one aspect, the invention provides a compound of formula IV, wherein R$_3$ is H. In one aspect, the invention provides a compound of formula IV, wherein R$_3$ is F. In one aspect, the invention provides a compound of formula IV, wherein one of R$_2$ or R$_3$ is H, and the remaining R$_2$ or R$_3$ is F. In one aspect, the invention provides a compound of formula IV, wherein R$_2$ is H and R$_3$ is F. In one aspect, the invention provides a compound of formula IV, wherein R$_2$ is F and R$_3$ is H. In one aspect, the invention provides a compound of formula IV, wherein R$_2$ and R$_3$ are both H. In one aspect, the invention provides a compound of formula IV, wherein R$_2$ and R$_3$ are both F. In one aspect, the invention provides a compound of formula IV, wherein R$_2$ and R$_3$ taken together with the carbon atom to which they are attached form a 4-membered heterocyclic ring. In one aspect, the invention provides a compound of formula IV, wherein the 4-membered heterocyclic ring is an oxetane ring. In one aspect, the invention provides a compound of formula IV, wherein the oxetane ring is an oxetan-3-yl ring. In one aspect, the invention provides a compound of formula IV, wherein the oxetane ring is an oxetan-2-yl ring.

In one aspect, the invention provides a compound of formula V:

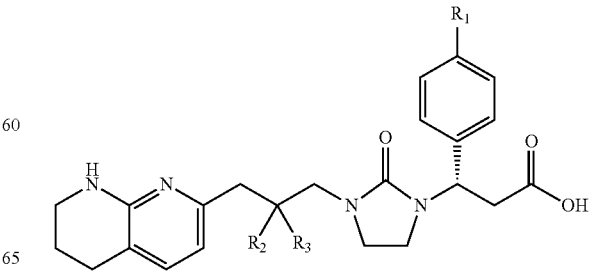

(V)

or a pharmaceutically acceptable salt or solvate thereof, wherein $R_1$ is $C_1$-$C_6$ alkoxy wherein said $C_1$-$C_6$ alkoxy is substituted with 0, 1, 2, 3, 4, or 5 fluorine atoms; and $R_2$ and $R_3$ are each independently selected from H and F, or $R_2$ and $R_3$ taken together with the carbon atom to which they are attached form a 3- or 4-membered carbocyclic or heterocyclic ring, provided that the compound of formula V contains at least one fluorine atom.

In one aspect, the invention provides a compound of formula V, wherein $R_1$ is $C_1$-$C_6$ alkoxy substituted with 1, 2, 3, 4, or 5 fluorine atoms. In one aspect, the invention provides a compound of formula V, wherein $R_1$ is $C_1$-$C_6$ alkoxy substituted with 2 or 3 fluorine atoms. In one aspect, the invention provides a compound of formula V, wherein $R_1$ is selected from $OCH_3$, $OCH_2F$, $OCHF_2$, $OCF_3$, and $OCH_2CH_3$. In one aspect, the invention provides a compound of formula V, wherein $R_1$ is selected from $OCH_2F$, $OCHF_2$, and $OCF_3$. In one aspect, the invention provides a compound of formula V, wherein $R_1$ is selected from $OCH_3$ and $OCH_2CH_3$. In one aspect, the invention provides a compound of formula V, wherein $R_1$ is selected from $OCH_3$ and $OCHF_2$. In one aspect, the invention provides a compound of formula V, wherein $R_1$ is $OCH_3$. In one aspect, the invention provides a compound of formula V, wherein $R_1$ is $OCHF_2$. In one aspect, the invention provides a compound of formula V, wherein $R_2$ is H. In one aspect, the invention provides a compound of formula V, wherein $R_2$ is F. In one aspect, the invention provides a compound of formula V, wherein $R_3$ is H. In one aspect, the invention provides a compound of formula V, wherein $R_3$ is F. In one aspect, the invention provides a compound of formula V, wherein one of $R_2$ or $R_3$ is H, and the remaining $R_2$ or $R_3$ is F. In one aspect, the invention provides a compound of formula V, wherein $R_2$ is H and $R_3$ is F. In one aspect, the invention provides a compound of formula V, wherein $R_2$ is F and $R_3$ is H. In one aspect, the invention provides a compound of formula V, wherein $R_2$ and $R_3$ are both H. In one aspect, the invention provides a compound of formula V, wherein $R_2$ and $R_3$ are both F. In one aspect, the invention provides a compound of formula V, wherein $R_2$ and $R_3$ taken together with the carbon atom to which they are attached form a 4-membered heterocyclic ring. In one aspect, the invention provides a compound of formula V, wherein the 4-membered heterocyclic ring is an oxetane ring. In one aspect, the invention provides a compound of formula V, wherein the oxetane ring is an oxetan-3-yl ring. In one aspect, the invention provides a compound of formula V, wherein the oxetane ring is an oxetan-2-yl ring.

[001] A compound of formula I:

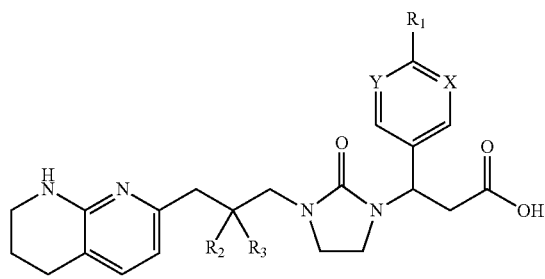

(I)

or a pharmaceutically acceptable salt or solvate thereof, wherein

X is selected from CH and N;
Y is selected from CH and N;

$R_1$ is $C_1$-$C_6$ alkoxy wherein said $C_1$-$C_6$ alkoxy is substituted with 0, 1, 2, 3, 4, or 5 fluorine atoms; and $R_2$ and $R_3$ are each independently selected from H and F, or $R_2$ and $R_3$ taken together with the carbon atom to which they are attached form a 3- or 4-membered carbocyclic or heterocyclic ring, provided that the compound of formula I contains at least one fluorine atom.

[002] A compound of formula II:

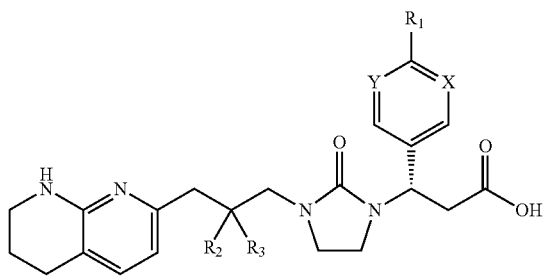

(II)

or a pharmaceutically acceptable salt or solvate thereof, wherein

X is selected from CH and N;
Y is selected from CH and N;

$R_1$ is $C_1$-$C_6$ alkoxy wherein said $C_1$-$C_6$ alkoxy is substituted with 0, 1, 2, 3, 4, or 5 fluorine atoms; and $R_2$ and $R_3$ are each independently selected from H and F, or $R_2$ and $R_3$ taken together with the carbon atom to which they are attached form a 3- or 4-membered carbocyclic or heterocyclic ring, provided that the compound of formula II contains at least one fluorine atom.

[003] A compound of paragraph [001] or [002], comprising a compound of formula I or II, wherein X is CH.

[004] A compound of paragraph [001] or [002], comprising a compound of formula I or II, wherein X is N.

[005] A compound of paragraph [001] or [002], comprising a compound of formula I or II, wherein Y is CH.

[006] A compound of paragraph [001] or [002], comprising a compound of formula I or II, wherein Y is N.

[007] A compound of paragraph [001] or [002], comprising a compound of formula I or II, wherein X or Y is CH and the remaining X or Y is N.

[008] A compound of paragraph [001] or [002], comprising a compound of formula I or II, wherein X is N and Y is CH.

[009] A compound of paragraph [001] or [002], comprising a compound of formula I or II, wherein X is CH and Y is N.

[010] A compound of paragraph [001] or [002], comprising a compound of formula I or II, wherein X and Y are both CH.

[111] A compound of paragraph [001] or [002], comprising a compound of formula I or II, wherein X and Y are both N

[012] A compound as in one of paragraphs [001] through [011], comprising a compound of formula I or II, wherein said $C_1$-$C_6$ alkoxy is substituted with 1, 2, 3, 4, or 5 fluorine atoms.

[013] A compound of paragraph [012], comprising a compound of formula I or II, wherein said $C_1$-$C_6$ alkoxy is substituted with 2 or 3 fluorine atoms.

[014] A compound as in one of paragraphs [001] through [011], comprising a compound of formula I or II, wherein $R_1$ is selected from $OCH_3$, $OCH_2F$, $OCHF_2$, $OCF_3$, and $OCH_2CH_3$.

[015] A compound of paragraph [013] or [014], comprising a compound of formula I or II, wherein $R_1$ is selected from $OCH_2F$, $OCHF_2$, and $OCF_3$.

[016] A compound of paragraph [014], comprising a compound of formula I or II, wherein $R_1$ is selected from $OCH_3$ and $OCH_2CH_3$.

[017] A compound of paragraph [014], comprising a compound of formula I or II, wherein $R_1$ is selected from $OCH_3$ and $OCHF_2$.

[018] A compound of paragraph [017], comprising a compound of formula I or II, wherein $R_1$ is $OCH_3$.

[019] A compound of paragraph [017], comprising a compound of formula I or II, wherein $R_1$ is $OCHF_2$.

[020] A compound as in one of paragraphs [001] through [019], comprising a compound of formula I or II, wherein $R_2$ is H.

[021] A compound as in one of paragraphs [001] through [019], comprising a compound of formula I or II, wherein $R_2$ is F.

[022] A compound as in one of paragraphs [001] through [019], comprising a compound of formula I or II, wherein $R_3$ is H.

[023] A compound as in one of paragraphs [001] through [019], comprising a compound of formula I or II, wherein $R_3$ is F.

[024] A compound as in one of paragraphs [001] through [019], comprising a compound of formula I or II, wherein one of $R_2$ or $R_3$ is H, and the remaining $R_2$ or $R_3$ is F.

[025] A compound as in one of paragraphs [001] through [019], comprising a compound of formula I or II, wherein $R_2$ is H and $R_3$ is F.

[026] A compound as in one of paragraphs [001] through [019], comprising a compound of formula I or II, wherein $R_2$ is F and $R_3$ is H.

[027] A compound as in one of paragraphs [001] through [019], comprising a compound of formula I or II, wherein $R_2$ and $R_3$ are both H.

[028] A compound as in one of paragraphs [001] through [019], comprising a compound of formula I or II, wherein $R_2$ and $R_3$ are both F.

[029] A compound as in one of paragraphs [001] through [019], comprising a compound of formula I or II, wherein $R_2$ and $R_3$ taken together with the carbon atom to which they are attached form a 4-membered heterocyclic ring.

[030] A compound of paragraph [029], comprising a compound of formula I or II, wherein the 4-membered heterocyclic ring is an oxetane ring.

[031] A compound of paragraph [030], comprising a compound of formula I or II, wherein the oxetane ring is an oxetan-3-yl ring.

[032] A compound of paragraph [030], comprising a compound of formula I or II, wherein the oxetane ring is an oxetan-2-yl ring.

[033] A compound of formula III:

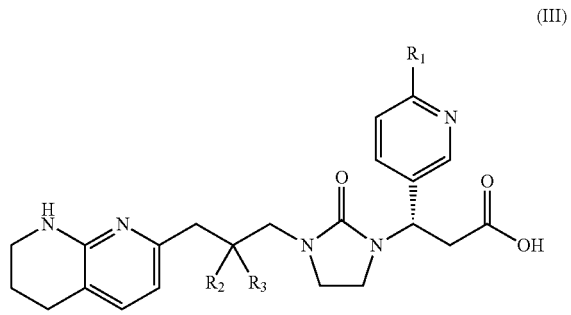

or a pharmaceutically acceptable salt or solvate thereof, wherein $R_1$ is $C_1$-$C_6$ alkoxy wherein said $C_1$-$C_6$ alkoxy is substituted with 0, 1, 2, 3, 4, or 5 fluorine atoms; and $R_2$ and $R_3$ are each independently selected from H and F, or $R_2$ and $R_3$ taken together with the carbon atom to which they are attached form a 3- or 4-membered carbocyclic or heterocyclic ring, provided that the compound of formula III contains at least one fluorine atom.

[034] A compound of paragraph [033], comprising a compound of formula III, wherein said $C_1$-$C_6$ alkoxy is substituted with 1, 2, 3, 4, or 5 fluorine atoms.

[035] A compound of paragraph [034], comprising a compound of formula III, wherein said $C_1$-$C_6$ alkoxy is substituted with 2 or 3 fluorine atoms.

[036] A compound of paragraph [033], comprising a compound of formula III, wherein $R_1$ is selected from $OCH_3$, $OCH_2F$, $OCHF_2$, $OCF_3$, and $OCH_2CH_3$.

[037] A compound of paragraph [035] or [036], comprising a compound of formula III, wherein $R_1$ is selected from $OCH_2F$, $OCHF_2$, and $OCF_3$.

[038] A compound of paragraph [036], comprising a compound of formula III, wherein $R_1$ is selected from $OCH_3$ and $OCH_2CH_3$.

[039] A compound of paragraph [036], comprising a compound of formula III, wherein $R_1$ is selected from $OCH_3$ and $OCHF_2$.

[040] A compound of paragraph [039], comprising a compound of formula III, wherein $R_1$ is $OCH_3$.

[041] A compound of paragraph [039], comprising a compound of formula III, wherein $R_1$ is $OCHF_2$.

[042] A compound as in one of paragraphs [033] through [041], comprising a compound of formula III, wherein $R_2$ is H.

[043] A compound as in one of paragraphs [033] through [041], comprising a compound of formula III, wherein $R_2$ is F.

[044] A compound as in one of paragraphs [033] through [041], comprising a compound of formula III, wherein $R_3$ is H.

[045] A compound as in one of paragraphs [033] through [041], comprising a compound of formula III, wherein $R_3$ is F.

[046] A compound as in one of paragraphs [033] through [041], comprising a compound of formula III, wherein one of $R_2$ or $R_3$ is H, and the remaining $R_2$ or $R_3$ is F.

[047] A compound as in one of paragraphs [033] through [041], comprising a compound of formula III, wherein $R_2$ is H and $R_3$ is F.

[048] A compound as in one of paragraphs [033] through [041], comprising a compound of formula III, wherein $R_2$ is F and $R_3$ is H.

[049] A compound as in one of paragraphs [033] through [041], comprising a compound of formula III, wherein $R_2$ and $R_3$ are both H.

[050] A compound as in one of paragraphs [033] through [041], comprising a compound of formula III, wherein $R_2$ and $R_3$ are both F.

[051] A compound as in one of paragraphs [033] through [041], comprising a compound of formula III, wherein $R_2$ and $R_3$ taken together with the carbon atom to which they are attached form a 4-membered heterocyclic ring.

[052] A compound of paragraph [051], comprising a compound of formula III, wherein the 4-membered heterocyclic ring is an oxetane ring.

[053] A compound of paragraph [052], comprising a compound of formula III, wherein the oxetane ring is an oxetan-3-yl ring.

[054] A compound of paragraph [052], comprising a compound of formula III, wherein the oxetane ring is an oxetan-2-yl ring.

[055] A compound of formula IV:

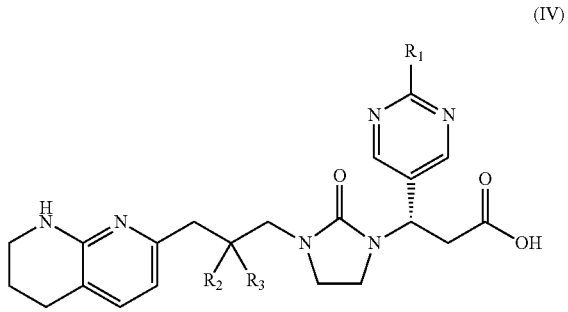

or a pharmaceutically acceptable salt or solvate thereof, wherein
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula IV contains at least one fluorine atom.

[056] A compound of paragraph [055], comprising a compound of formula IV, wherein said $C_1$-$C_6$ alkoxy is substituted with 1, 2, 3, 4, or 5 fluorine atoms.

[057] A compound of paragraph [056], comprising a compound of formula IV, wherein said $C_1$-$C_6$ alkoxy is substituted with 2 or 3 fluorine atoms.

[058] A compound of paragraph [055], comprising a compound of formula IV, wherein $R_1$ is selected from $OCH_3$, $OCH_2F$, $OCHF_2$, $OCF_3$, and $OCH_2CH_3$.

[059] A compound of paragraph [057] or [058], comprising a compound of formula IV, wherein $R_1$ is selected from $OCH_2F$, $OCHF_2$, and $OCF_3$.

[060] A compound of paragraph [058], comprising a compound of formula IV, wherein $R_1$ is selected from $OCH_3$ and $OCH_2CH_3$.

[061] A compound of paragraph [058], comprising a compound of formula IV, wherein $R_1$ is selected from $OCH_3$ and $OCHF_2$.

[062] A compound of paragraph [061], comprising a compound of formula IV, wherein $R_1$ is $OCH_3$.

[063] A compound of paragraph [061], comprising a compound of formula IV, wherein $R_1$ is $OCHF_2$.

[064] A compound as in one of paragraphs [055] through [063], comprising a compound of formula IV, wherein $R_2$ is H.

[065] A compound as in one of paragraphs [055] through [063], comprising a compound of formula IV, wherein $R_2$ is F.

[066] A compound as in one of paragraphs [055] through [063], comprising a compound of formula IV, wherein $R_3$ is H.

[067] A compound as in one of paragraphs [055] through [063], comprising a compound of formula IV, wherein $R_3$ is F.

[068] A compound as in one of paragraphs [055] through [063], comprising a compound of formula IV, wherein one of $R_2$ or $R_3$ is H, and the remaining $R_2$ or $R_3$ is F.

[069] A compound as in one of paragraphs [055] through [063], comprising a compound of formula IV, wherein $R_2$ is H and $R_3$ is F.

[070] A compound as in one of paragraphs [055] through [063], comprising a compound of formula IV, wherein $R_2$ is F and $R_3$ is H.

[071] A compound as in one of paragraphs [055] through [063], comprising a compound of formula IV, wherein $R_2$ and $R_3$ are both H.

[072] A compound as in one of paragraphs [055] through [063], comprising a compound of formula IV, wherein $R_2$ and $R_3$ are both F.

[073] A compound as in one of paragraphs [055] through [063], comprising a compound of formula IV, wherein $R_2$ and $R_3$ taken together with the carbon atom to which they are attached form a 4-membered heterocyclic ring.

[074] A compound of paragraph [073], comprising a compound of formula IV, wherein the 4-membered heterocyclic ring is an oxetane ring.

[075] A compound of paragraph [074], comprising a compound of formula IV, wherein the oxetane ring is an oxetan-3-yl ring.

[076] A compound of paragraph [074], comprising a compound of formula IV, wherein the oxetane ring is an oxetan-2-yl ring.

[077] A compound of formula V:

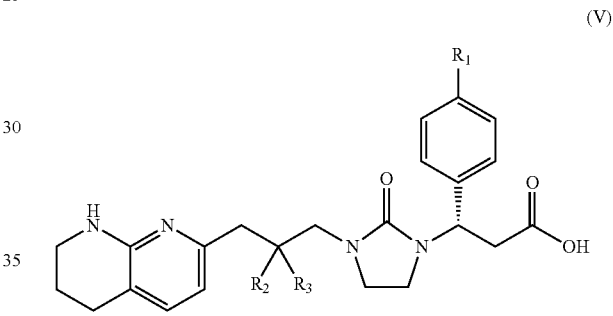

or a pharmaceutically acceptable salt or solvate thereof, wherein
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula V contains at least one fluorine atom.

[078] A compound of paragraph [077], comprising a compound of formula V, wherein said $C_1$-$C_6$ alkoxy is substituted with 1, 2, 3, 4, or 5 fluorine atoms.

[079] A compound of paragraph [078], comprising a compound of formula V, wherein said $C_1$-$C_6$ alkoxy is substituted with 2 or 3 fluorine atoms.

[080] A compound of paragraph [077], comprising a compound of formula V, wherein $R_1$ is selected from $OCH_3$, $OCH_2F$, $OCHF_2$, $OCF_3$, and $OCH_2CH_3$.

[081] A compound of paragraph [079] or [080], comprising a compound of formula V, wherein $R_1$ is selected from $OCH_2F$, $OCHF_2$, and $OCF_3$.

[082] A compound of paragraph [080], comprising a compound of formula V, wherein $R_1$ is selected from $OCH_3$ and $OCH_2CH_3$.

[083] A compound of paragraph [080], comprising a compound of formula V, wherein $R_1$ is selected from $OCH_3$ and $OCHF_2$.

[084] A compound of paragraph [083], comprising a compound of formula V, wherein $R_1$ is $OCH_3$.

[085] A compound of paragraph [083], comprising a compound of formula V, wherein $R_1$ is $OCHF_2$.

[086] A compound as in one of paragraphs [077] through [085], comprising a compound of formula V, wherein $R_2$ is H.

[087] A compound as in one of paragraphs [077] through [085], comprising a compound of formula V, wherein $R_2$ is F.

[088] A compound as in one of paragraphs [077] through [085], comprising a compound of formula V, wherein $R_3$ is H.

[089] A compound as in one of paragraphs [077] through [085], comprising a compound of formula V, wherein $R_3$ is F.

[090] A compound as in one of paragraphs [077] through [085], comprising a compound of formula V, wherein one of $R_2$ or $R_3$ is H, and the remaining $R_2$ or $R_3$ is F.

[091] A compound as in one of paragraphs [077] through [085], comprising a compound of formula V, wherein $R_2$ is H and $R_3$ is F.

[092] A compound as in one of paragraphs [077] through [085], comprising a compound of formula V, wherein $R_2$ is F and $R_3$ is H.

[093] A compound as in one of paragraphs [077] through [085], comprising a compound of formula V, wherein $R_2$ and $R_3$ are both H.

[094] A compound as in one of paragraphs [077] through [085], comprising a compound of formula V, wherein $R_2$ and $R_3$ are both F.

[095] A compound as in one of paragraphs [077] through [085], comprising a compound of formula V, wherein $R_2$ and $R_3$ taken together with the carbon atom to which they are attached form a 4-membered heterocyclic ring.

[096] A compound of paragraph [095], comprising a compound of formula V, wherein the 4-membered heterocyclic ring is an oxetane ring.

[097] A compound of paragraph [096], comprising a compound of formula V, wherein the oxetane ring is an oxetan-3-yl ring.

[098] A compound of paragraph [096], comprising a compound of formula V, wherein the oxetane ring is an oxetan-2-yl ring.

[099] A compound selected from:

| Compound # | Chemical Structure |
| --- | --- |
| A1 | 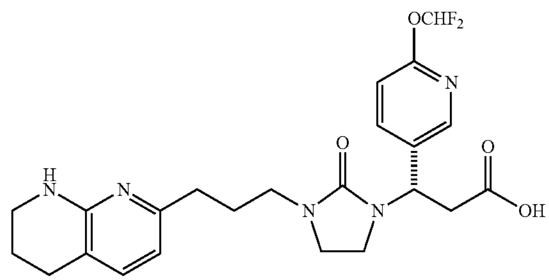 [SMILES: O=C(O)C[C@@H](c1ccc(OC(F)F)nc1)N1CCN(CCCc2ccc3c(n2)NCCC3)C1=O] |
| A2 | 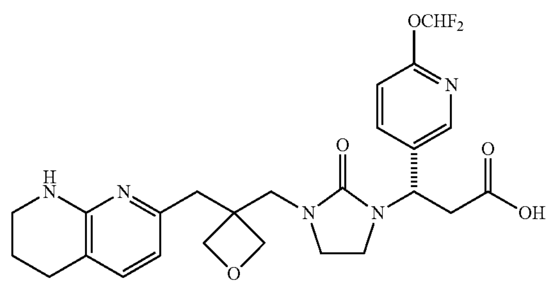 [SMILES: O=C(O)C[C@@H](c1ccc(OC(F)F)nc1)N1CCN(CC2(Cc3ccc4c(n3)NCCC4)COC2)C1=O] |
| A3 | 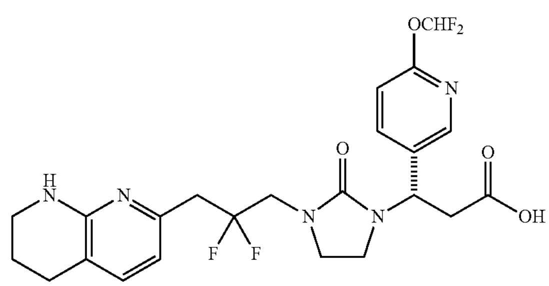 [SMILES: O=C(O)C[C@@H](c1ccc(OC(F)F)nc1)N1CCN(CC(F)(F)Cc2ccc3c(n2)NCCC3)C1=O] |
| A4 | 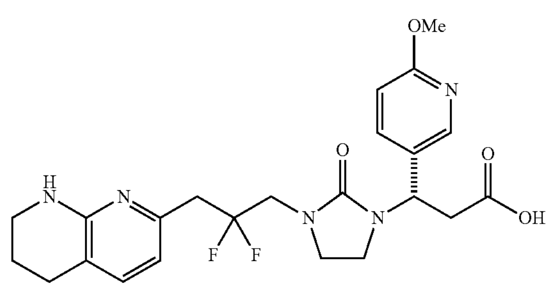 |

-continued

| Compound # | Chemical Structure |
|---|---|
| A5 | 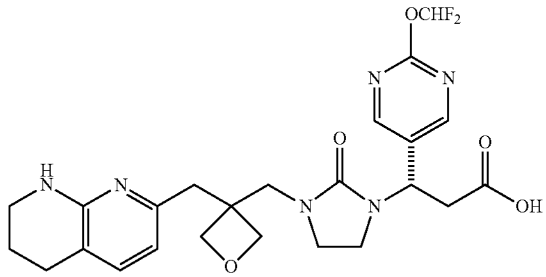 [SMILES: O=C(O)C[C@@H](c1cnc(OC(F)F)nc1)N1CCN(CC2(Cc3ccc4c(n3)NCCC4)COC2)C1=O] |
| A6 | 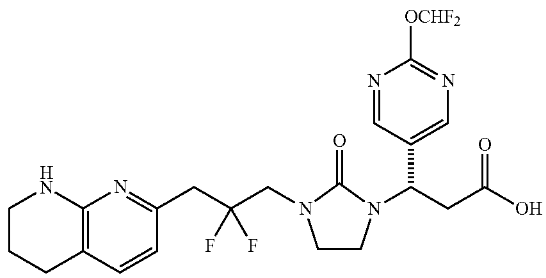 |
| A7 | 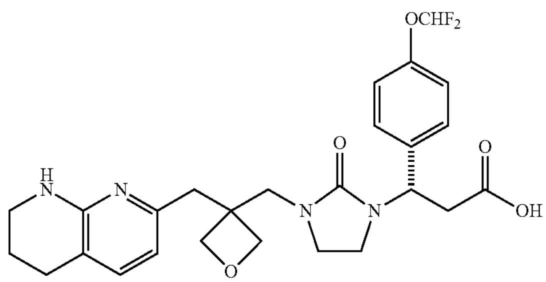 [SMILES: O=C(O)C[C@@H](c1ccc(OC(F)F)cc1)N1CCN(CC2(Cc3ccc4c(n3)NCCC4)COC2)C1=O] |
| A8 | | or a pharmaceutically acceptable salt or solvate thereof.

[100] A pharmaceutical composition comprising a compound or a pharmaceutically acceptable salt or solvate thereof as in one of paragraphs [001] through [099] and a pharmaceutical carrier, diluent, or excipient.

[101] The composition of paragraph [100] which further comprises an active ingredient selected from the group consisting of
a) an organic bisphosphonate or a pharmaceutically acceptable salt or ester thereof,
b) an estrogen receptor modulator,
c) a cytotoxic/antiproliferative agent,
d) a matrix metalloproteinase inhibitor,
e) an inhibitor of epidermal-derived, fibroblast-derived, or platelet-derived growth factors,
f) an inhibitor of VEGF,
g) an inhibitor of Flk-1/KDR, Flt-1, Tck/Tie-2, or Tie-1,
h) a cathepsin K inhibitor, and
i) a prenylation inhibitor, such as a farnesyl transferase inhibitor or a geranylgeranyl transferase inhibitor or a dual farnesyl/geranylgeranyl transferase inhibitor; and mixtures thereof.

[102] The composition of paragraph [101] wherein said active ingredient is selected from the group consisting of
a) an organic bisphosphonate or a pharmaceutically acceptable salt or ester thereof,
b) an estrogen receptor modulator, and
c) a cathepsin K inhibitor; and mixtures thereof.

[103] The composition of paragraph [102] wherein said organic bisphosphonate or pharmaceutically acceptable salt or ester thereof is alendronate monosodium trihydrate.

[104] The composition of paragraph [101] wherein said active ingredient is selected from the group consisting of
a) a cytotoxic/antiproliferative agent,
b) a matrix metalloproteinase inhibitor,
c) an inhibitor of epidermal-derived, fibroblast-derived, or platelet-derived growth factors, d) an inhibitor of VEGF, and
e) an inhibitor of Flk-1/KDR, Flt-1, Tck/Tie-2, or Tie-1; and mixtures thereof.

[105] A method of eliciting an integrin receptor antagonizing effect in a subject in need thereof, comprising administering to the subject a therapeutically effective amount of a compound or a pharmaceutically acceptable salt or solvate as in one of paragraphs [001] through [099].

[106] The method of paragraph [105] wherein the integrin receptor antagonizing effect is an αvβ3 antagonizing effect.

[107] The method of paragraph [106] wherein the αvβ3 antagonizing effect is selected from the group consisting of inhibition of bone resorption, restenosis, angiogenesis, diabetic retinopathy, macular degeneration, inflammation, viral disease, tumor growth, and metastasis.

[108] The method of paragraph [107] wherein the αvβ3 antagonizing effect is the inhibition of bone resorption.

[109] The method of paragraph [105] wherein the integrin receptor antagonizing effect is an αvβ5 antagonizing effect.

[110] The method of paragraph [109] wherein the αvβ5 antagonizing effect is selected from the group consisting of inhibition of restenosis, angiogenesis, diabetic retinopathy, macular degeneration, inflammation, tumor growth, and metastasis.

[111] The method of paragraph [105] wherein the integrin receptor antagonizing effect is a dual αvβ3/αvβ5 antagonizing effect.

[112] The method of paragraph [111] wherein the dual αvβ3/αvβ5 antagonizing effect is selected from the group consisting of inhibition of bone resorption, restenosis, angiogenesis, diabetic retinopathy, macular degeneration, inflammation, viral disease, tumor growth, and metastasis.

[113] The method of paragraph [105] wherein the integrin antagonizing effect is an αvβ6 antagonizing effect.

[114] The method of paragraph [113] wherein the αvβ6 antagonizing effect is selected from the group consisting of angiogenesis, inflammatory response, and wound healing.

[115] A method of eliciting an integrin receptor antagonizing effect in a subject in need thereof, comprising administering to the subject a therapeutically effective amount of the composition of paragraph [100].

[116] A method of treating and/or preventing a condition in a subject comprising administering to the subject in need thereof an effective amount of a compound or a pharmaceutically acceptable salt or solvate thereof as in one of paragraphs [001] through [099].

[117] The method of paragraph [116], wherein the condition is mediated by antagonism of an integrin receptor.

[118] A method of inhibiting bone resorption in a subject in need thereof, comprising administering to the subject a therapeutically effective amount of the composition of paragraph [100].

[119] A method of inhibiting bone resorption in a subject in need thereof, comprising administering to the subject a therapeutically effective amount of the composition of paragraph [102].

[120] A method of treating tumor growth in a subject in need thereof, comprising administering to the subject a therapeutically effective amount of the composition of paragraph [104].

[121] A method of treating tumor growth in a subject in need thereof, comprising administering to the subject a therapeutically effective amount of a compound as in one of paragraphs [001] through [099] in combination with radiation therapy.

[122] A method of synthesizing a compound or a pharmaceutically acceptable salt or solvate thereof as in one of paragraphs [001] through [099].

In one aspect, the invention provides a compound or a pharmaceutically acceptable salt or solvate thereof of Table 1.

TABLE 1

| Compound # | Chemical Structure |
| --- | --- |
| A1 | 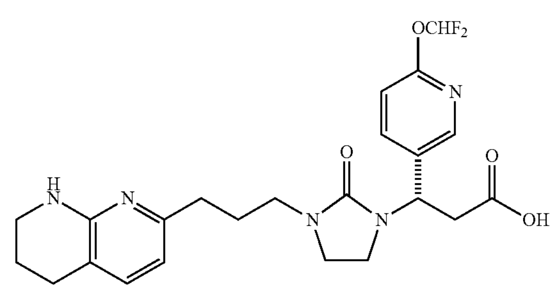 [SMILES: O=C(O)C[C@@H](c1ccc(OC(F)F)nc1)N1CCN(CCCc2ccc3c(n2)NCCC3)C1=O] |
| A2 | 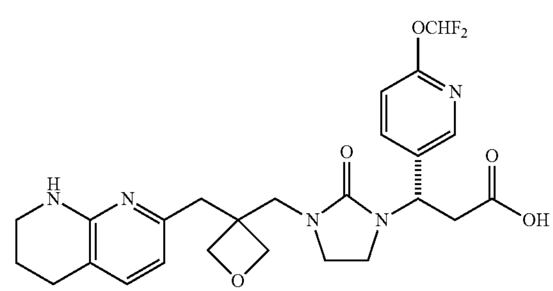 [SMILES: O=C(O)C[C@@H](c1ccc(OC(F)F)nc1)N1CCN(CC2(Cc3ccc4c(n3)NCCC4)COC2)C1=O] |

TABLE 1-continued

| Compound # | Chemical Structure |
| --- | --- |
| A3 | 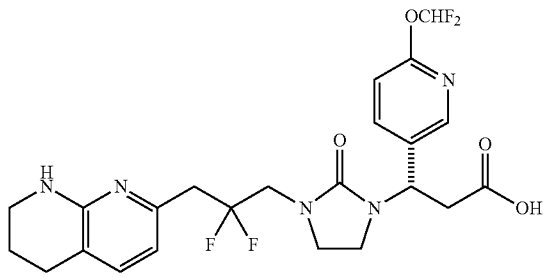 [SMILES: O=C(O)C[C@@H](c1ccc(OC(F)F)nc1)N1CCN(CC(F)(F)Cc2ccc3c(n2)NCCC3)C1=O] |
| A4 | 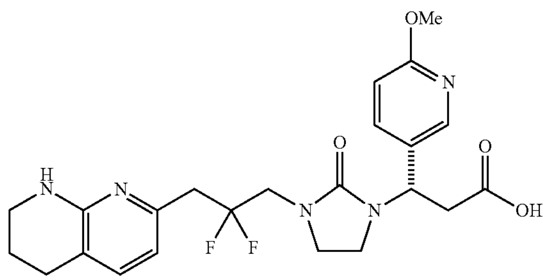 [SMILES: COc1ccc([C@H](CC(=O)O)N2CCN(CC(F)(F)Cc3ccc4c(n3)NCCC4)C2=O)cn1] |
| A5 | 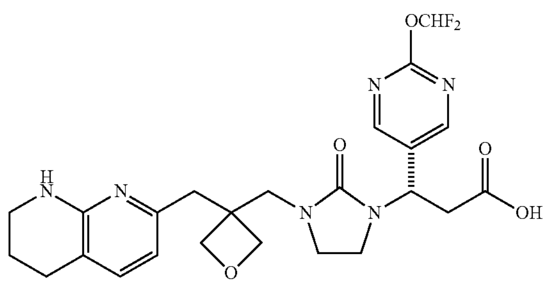 [SMILES: O=C(O)C[C@@H](c1cnc(OC(F)F)nc1)N1CCN(CC2(Cc3ccc4c(n3)NCCC4)COC2)C1=O] |
| A6 | 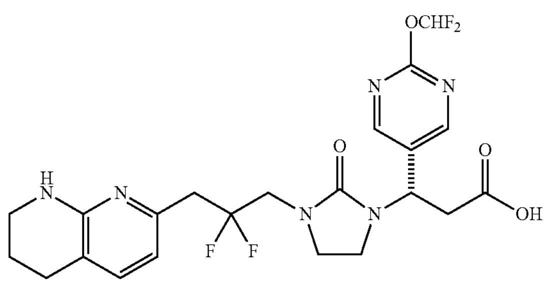 |
| A7 | 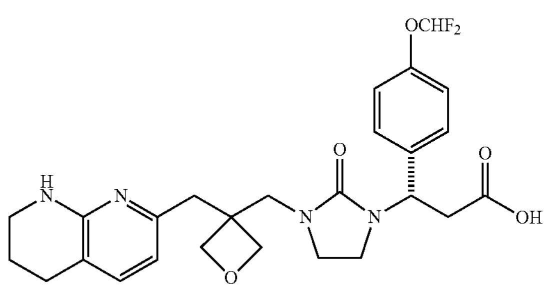 [SMILES: O=C(O)C[C@@H](c1ccc(OC(F)F)cc1)N1CCN(CC2(Cc3ccc4c(n3)NCCC4)COC2)C1=O] |

TABLE 1-continued

| Compound # | Chemical Structure |
|---|---|
| A8 | 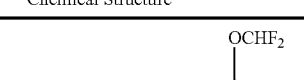 |

In one aspect, a compound of the invention is a pharmaceutically acceptable salt. In one aspect, a compound of the invention is a solvate. In one aspect, a compound of the invention is a hydrate.

The invention relates to pharmaceutical compositions comprising one of the compounds of the invention as an active ingredient. In one aspect, the invention provides a pharmaceutical composition comprising at least one compound of formula I, II, III, IV, or V or a pharmaceutically acceptable salt or solvate thereof and one or more pharmaceutically acceptable carriers, diluents, or excipients. In one aspect, the invention provides a pharmaceutical composition comprising at least one compound of Table 1.

In one aspect, the invention relates to a method of synthesizing a compound of the invention or a pharmaceutically acceptable salt or solvate thereof.

The invention also comprehends deuterium labeled compounds of formula I, II, III, IV, and V and the compounds listed in Table 1. The deuterium labeled compounds comprise a deuterium atom having an abundance of deuterium that is substantially greater than the natural abundance of deuterium, which is 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of formula I, II, III, IV, and V and the compounds listed in Table 1 of the invention can generally be prepared by carrying out the procedures disclosed in the Schemes and/or in the Examples described herein, by substituting a readily available deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with heavier deuterium, i.e., $^2$H, can afford certain therapeutic advantages resulting from greater metabolic stability, for example increased in vivo half-life or reduced dosage requirements.

Methods of Use

Representative compounds of the invention typically display submicromolar affinity for the integrin receptors, particularly the αvβ3, αvβ5 and/or αvβ36 receptors. Compounds of the invention are therefore useful for treating a subject suffering from a bone condition caused or mediated by increased bone resorption, who are in need of such therapy. Pharmacologically effective amounts of the compounds, including pharmaceutically acceptable salts thereof, are administered to the subject, to inhibit the activity of mammalian osteoclasts.

The compounds of the invention are administered in dosages effective to antagonize the αvβ3 receptor where such treatment is needed, as, for example, in the prevention or treatment of osteoporosis.

Further exemplifying the invention is the method wherein the integrin receptor antagonizing effect is an αvβ3 antagonizing effect. An illustration of the invention is the method wherein the αvβ3 antagonizing effect is selected from inhibition of bone resorption, restenosis, angiogenesis, diabetic retinopathy, macular degeneration, inflammation, viral disease, tumor growth, or metastasis. In one aspect, the αvβ3 antagonizing effect is the inhibition of bone resorption.

An example of the invention is the method wherein the integrin reception antagonizing effect is an αvβ5 antagonizing effect. More specifically, the αvβ5 antagonizing effect is selected from inhibition of restenosis, angiogenesis, diabetic retinopathy, macular degeneration, inflammation, tumor growth, or metastasis.

Illustrating the invention is the method wherein the integrin receptor antagonizing effect is a dual αvβ3/αvβ5 antagonizing effect. More particularly, the dual αvβ3/αvβ5 antagonizing is selected from inhibition of bone resorption, restenosis, angiogenesis, diabetic retinopathy, macular degeneration, inflammation, viral disease, tumor growth, or metastasis.

Illustrating the invention is the method wherein the integrin receptor antagonizing effect is an αvβ6 antagonizing effect. More particularly, the αvβ6 antagonizing effect is selected from inhibition of angiogenesis, inflammatory response, or wound healing.

Illustrating the invention is the method wherein the αvβ3 antagonizing effect is selected from inhibition of bone resorption, inhibition of restenosis, inhibition of angiogenesis, inhibition of diabetic retinopathy, inhibition of macular degeneration, inhibition of atherosclerosis, inflammation, viral disease, or inhibition of tumor growth or metastasis. In one aspect, the αvβ3 antagonizing effect is the inhibition of bone resorption.

More particularly illustrating the invention is a pharmaceutical composition comprising any of the compounds described above and a pharmaceutically acceptable carrier.

Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Illustrating the invention is a method of treating and/or preventing a condition in a subject in need thereof, comprising administering to the subject a therapeutically effective amount of any of the compounds described above. Further illustrating the invention is a method of treating and/or preventing a condition mediated by antagonism of an integrin receptor in a subject in need thereof, comprising administering to the subject a therapeutically effective amount of any of the compounds described above. In one aspect, the condition is selected from bone resorption, osteoporosis, restenosis, diabetic retinopathy, macular degeneration, angiogenesis, atherosclerosis, inflammation, viral disease, cancer, tumor growth, and metastasis. In one aspect, the condition is selected from osteoporosis and cancer. In one aspect, the condition is osteoporosis.

More specifically exemplifying the invention is a method of eliciting an integrin antagonizing effect in a subject in need thereof, comprising administering to the subject a therapeutically effective amount of any of the compounds or any of the pharmaceutical compositions described above. In one aspect, the integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of viral disease, or inhibition of tumor growth or metastasis. In one aspect, the αvβ3 antagonizing effect is inhibition of bone resorption. Alternatively, the integrin antagonizing effect is an αvβ5 antagonizing effect, an αvβ6 antagonizing effect, or a mixed αvβ3, αvβ5, and αvβ6 antagonizing effect. Examples of αvβ35 antagonizing effects are inhibition of restenosis, atherosclerosis, angiogenesis, diabetic retinopathy, macular degeneration, inflammation, viral disease, or tumor growth. Examples of dual αvβ6 antagonizing effects are inhibition of angiogenesis, inflammatory response and wound healing.

Additional examples of the invention are methods of inhibiting bone resorption and of treating and/or preventing osteoporosis in a subject in need thereof, comprising administering to the subject a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a subject in need thereof, comprising administering to the subject a therapeutically effective amount of any of the compounds or any of the pharmaceutical compositions described above.

More particularly exemplifying the invention is the use of any of the compounds described above in the preparation of a medicament for the treatment and/or prevention of osteoporosis in a subject in need thereof. Still further exemplifying the invention is the use of any of the compounds described above in the preparation of a medicament for the treatment and/or prevention of bone resorption, tumor growth, cancer, restenosis, atherosclerosis, diabetic retinopathy, macular degeneration, inflammation, viral disease, and/or angiogenesis.

Also exemplifying the invention are compositions further comprising an active ingredient selected from the group consisting of
a.) an organic bisphosphonate or a pharmaceutically acceptable salt or ester thereof,
b.) an estrogen receptor modulator,
c.) a cytototoxic/antiproliferative agent,
d.) a matrix metalloproteinase inhibitor,
e.) an inhibitor of epidermal-derived, fibroblast-derived, or platelet-derived growth factors,
f.) an inhibitor of VEGF,
g.) an inhibitor of Flk-1/KDR, Flt-1, Tck/Tie-2, or Tie-1,
h.) a cathespin K inhibitor; and
i.) a prenylation inhibitor, such as a farnesyl transferase inhibitor or a geranylgeranyl transferase inhibitor or a dual farnesyl/geranylgeranyl transferase inhibitor, and mixtures thereof.

(See, B. Millauer et al., "Dominant-Negative Inhibition of Flk-1 Suppresses the Growth of Many Tumor Types in Vivo", *Cancer Research* 56, 161514 1620 (1996), which is incorporated by reference herein in its entirety).

In one aspect, the active ingredient is selected from the group consisting of:
a.) an organic bisphosphonate or a pharmaceutically acceptable salt or ester thereof,
b.) an estrogen receptor modulator, and
c.) a cathepsin K inhibitor, and mixtures thereof Nonlimiting examples of such bisphosphonates include alendronate, etidronate, pamidronate, risedronate, ibandronate, and pharmaceutically acceptable salts and esters thereof. In one aspect the bisphosphonate is alendronate, e.g. alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling, At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

The invention is also directed to combinations of the compounds of the invention with one or more agents useful in the prevention or treatment of osteoporosis. For example, the compounds of the instant invention may be effectively administered in combination with effective amounts of other agents such as an organic bisphosphonate, an estrogen receptor modulator, or a cathepsin K inhibitor.

Additional illustrations of the invention are methods of inhibiting bone resorption in a subject in need thereof, comprising administering to the subject a therapeutically effective amount of a compound described above and one or more agents described above. Additional illustrations of the invention are methods of treating tumor growth in a subject in need thereof, comprising administering to the subject a therapeutically effective amount of a compound described above and one or more agents known to be cytotoxic/antiproliferative. Also, the compounds of the invention can be administered in combination with radiation therapy for treating tumor growth and metastasis.

In addition, the integrin αvβ3 antagonist compounds of the invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the invention would be useful in increasing bone mass in patients with growth hormone deficiency. Thus, in one aspect, combinations are simultaneous or alternating treatments of an αvβ3 receptor antagonist of the invention and a growth hormone secretagogue, optionally including a third component comprising an organic bisphosphonate, e.g. alendronate monosodium trihydrate.

In accordance with the method of the invention, the individual components of the combination can be administered separately at different times during the course of therapy or concurrently in divided or single combination forms. The instant invention is therefore to be understood as embracing all such regimens of simultaneous or alternating treatment, and the term "administering" is to be interpreted accordingly. It will be understood that the scope of combinations of the compounds of the invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or in-fusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the invention is selected in accordance with a variety of factors including type, species, age, weight, sex and medical condition of the patient; the severity of the condition to be treated; the routes of administration; the renal and hepatic function of the patient; and the particular compound or salt thereof employed. An ordinary skilled physician, veterinarian or clinician can readily determine and prescribe the effective amount of the drug required to prevent, counter or arrest the progress of the condition.

Oral dosages of the invention, when used for the indicated effects, will range between about 0.01 mg per kg of body weight per day (mg/kg/day) to about 100 mg/kg/day, 0.01 to 10 mg/kg/day, and 0.1 to 5.0 mg/kg/day. For oral administration, the compositions are provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, from about 1 mg to about 100 mg of active ingredient. Intravenously, doses will range from about 0.1 to about 10 mg/kg/minute during a constant rate infusion. Advantageously, compounds of the invention may be administered in a single daily dose, or the total daily dosage may be administered in divided doses of two, three or four times daily. Furthermore, compounds of the invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the invention may also be delivered by the use of monoclonal antibodies as individual carriers to which the compound molecules are coupled. The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol or polyethyleneoxide-polylysine substituted with palmitoyl residues. Furthermore, the compounds of the invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

EXAMPLES
Experimental Procedures and Compound Characterization
Example 1
Synthesis of (S)-3-(6-(difluoromethoxy)4lyridine-3-yl)-3-(2-oxo-3-(3-(5,6,7,8-tetrahydro-1,8-naphthyridin-2-yl)propyl)imidazolidin-1-yl)propanoic acid (Compound A1 in Table 1)
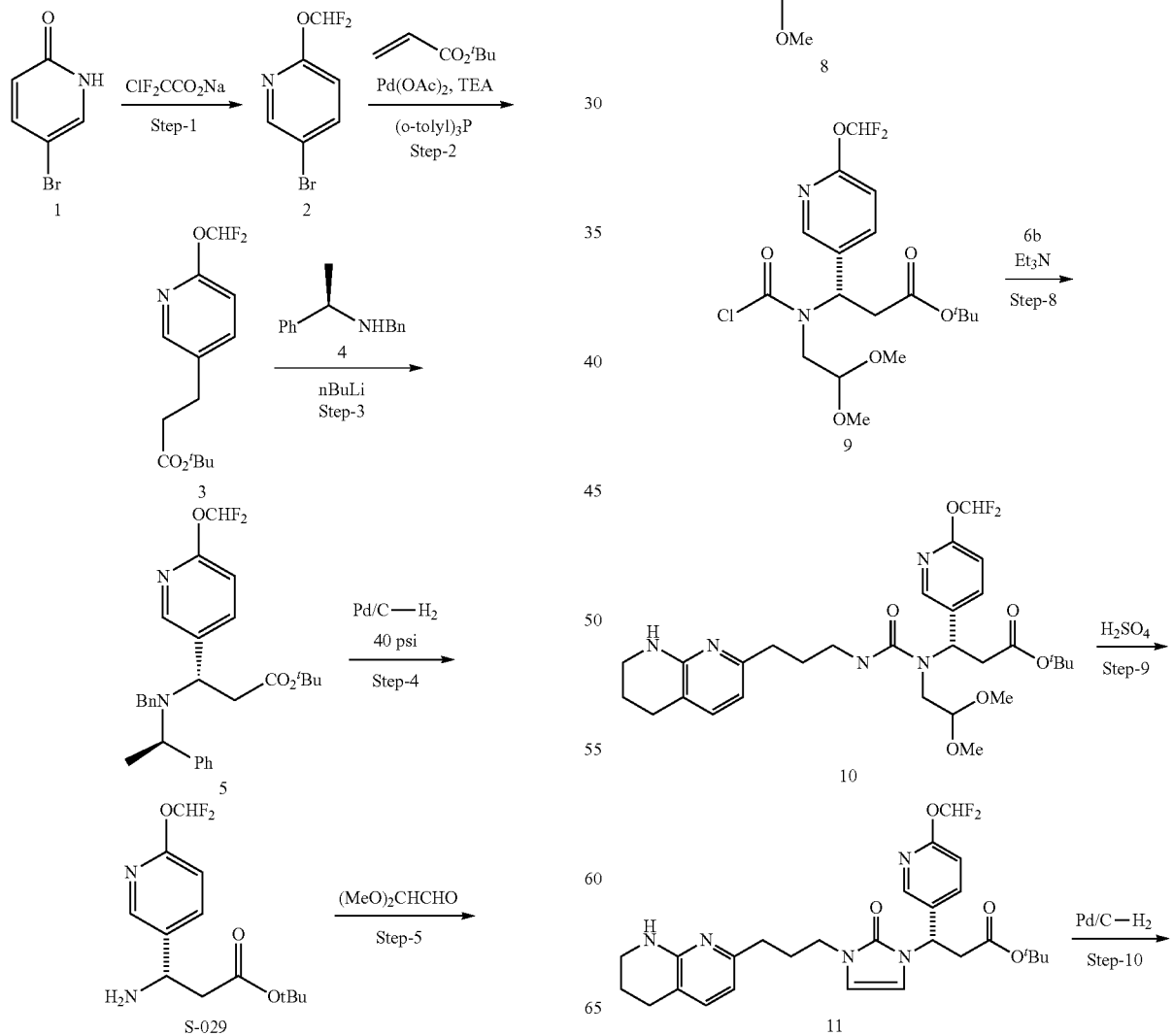

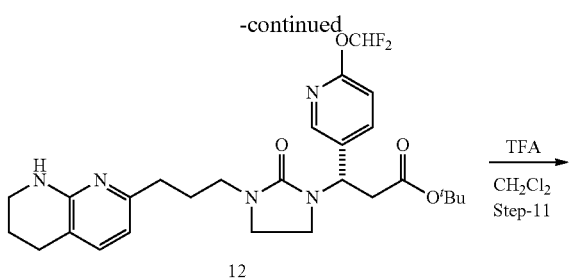

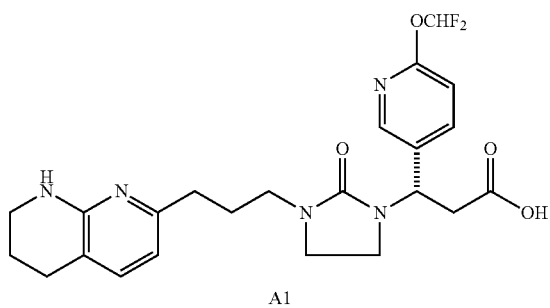

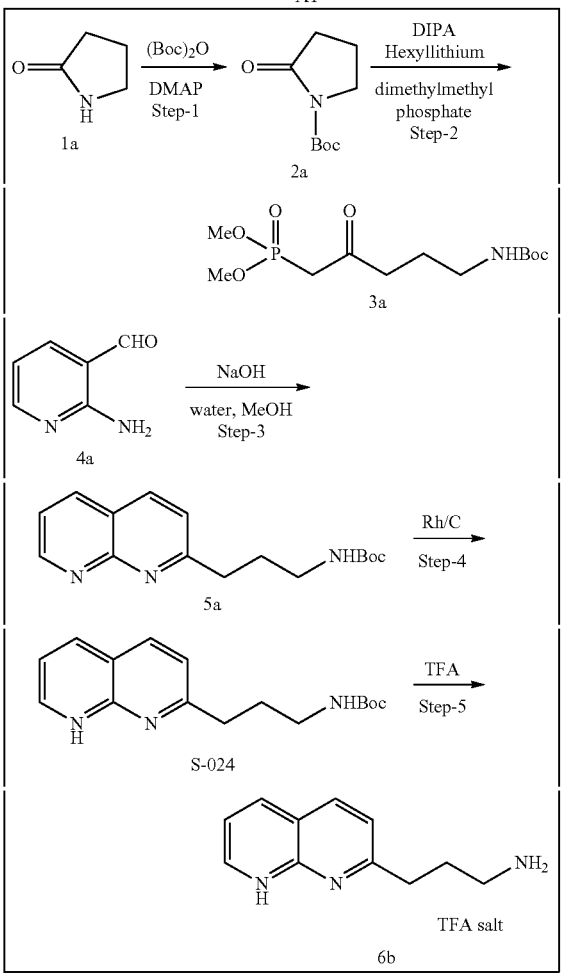

Experimental Details:

tert-butyl 2-oxopyrrolidine-1-carboxylate (2a)

To a stirred solution of compound 1a (10.0 g, 117 mmol, 1.0 equiv.) in DCM, (Boc)$_2$O (25.5 g, 117 mmol, 1.00 equiv.) and DMAP (0.022 g, 0.180 mmol, 0.001 equiv.) were added at RT and stirred for 12 h. After consumption of the starting material (monitored by TLC), volatiles were removed under reduced pressure to afford compound 2a (19.6 g, 90.3%) as a brown syrup. TLC: 50% EtOAc/Hexane (R$_f$: 0.40)

$^1$H NMR (400 MHz, CDCl$_3$): δ 3.74 (t, J=6.8 Hz, 2H), 2.50 (t, J=8.0 Hz, 2H), 2.01 (t, J=7.6 Hz, 2H), 1.52 (s, 9H)

tert-butyl(5-(dimethoxyphosphoryl)-4-oxopentyl)carbamate (3a)

To a stirred solution of iPr$_2$NH (2.99 mL, 21.8 mmol, 1.35 equiv.) in THF, cooled to −10° C., Hexyl Lithium (8.79 mL, 20.0 mmol, 1.24 equiv.) was slowly added. The reaction mixture was cooled to −60° C., Dimethylmethyl phosphonate (2.20 mL, 20.9 mmol, 1.29 equiv.) was added and stirred for 1 h, the temperature was raised to −40° C., compound 2a (3.0 g, 16.2 mmol, 1.0 equiv.) was introduced to the reaction mixture and stirring was continued for further 1 h. After consumption of the starting material, 2N H$_2$SO$_4$ solution (20 mL) was added slowly to the reaction and stirred at 0° C. for 15 minutes. The aqueous layer was extracted with EtOAc (2×25 mL). The combined organic extracts were washed with water (25 mL), brine (25 ml), dried over Na$_2$SO$_4$, filtered and evaporated under reduced pressure to afford compound 3a as a brown liquid (5.0 g, crude).

TLC: 80% EtOAc/Hexane (R$_f$: 0.30)

$^1$H NMR (400 MHz, CDCl$_3$): δ 4.85 (brs, 1H, Exc), 3.80-3.72 (m, 8H), 3.13-3.07 (m, 2H), 2.67 (t, J=6.8 Hz, 2H), 1.87-1.76 (m, 2H), 1.43 (s, 9H)

LC-MS: m/z=308.3 [M+H]$^+$ at RT 2.67 (99.1% purity)

tert-butyl(3-(1,8-naphthyridin-2-yl)propyl)carbamate (5a)

To a stirred solution of compound 4a (0.500 g, 4.09 mmol, 1.0 equiv.) and compound 3a (1.26 g, crude, 1.0 equiv.) in MeOH (9.17 mL), 50% NaOH solution (0.314 mL) was added and the reaction mixture was stirred at 50° C. for 10 h. After consumption of the starting material (by TLC), volatiles were removed, crude residue was diluted with EtOAc (15 mL) and the organic layer was washed with water (2×15 mL). The separated organic layer was dried over Na$_2$SO$_4$, filtered and concentrated under reduced pressure to afford brown syrup, which was purified by column chromatography on neutral alumina (80% EtOAc: Hexane) to provide compound 5a (0.980 g, 83.3%) as an off-white solid.

TLC: EtOAc $^1$H NMR (500 MHz, CDCl$_3$): δ 9.09 (s, 1H), 8.17-8.15 (m, 1H), 8.10 (d, J=8.0 Hz, 1H), 7.45 (t, J=8.0 Hz, 1H), 7.41 (t, J=15.0, 1H), 4.76 (brs, 1H, Exc), 3.25-3.21 (m, 2H), 3.09 (t, J=10.0 Hz, 2H), 2.14-2.08 (m, 2H), 1.42 (s, 9H)

LC-MS: m/z=288 [M−H]$^-$ at RT 2.86 (94.7%)

tert-butyl(3-(5,6,7,8-tetrahydro-1,8-naphthyridin-2-yl)propyl)carbamate (S-024)

To a stirred solution of compound 5a (0.25 g, 0.87 mmol, 1.00 equiv.) in MeOH (5 mL), Rh/C (catalytic, 5 wt %) was added under N$_2$ atmosphere and stirred at RT for 8 h under hydrogen (balloon pressure) atmosphere. After completion of the starting material, the reaction mixture was filtered through pad of celite, washed with MeOH (5 mL). The filtrate was evaporated under reduced pressure to afford compound S-024 (0.18 g, 71.1%) as a white solid.

TLC: EtOAc $^1$H NMR (400 MHz, CDCl$_3$): δ 7.05 (d, J=7.6 Hz, 1H), 6.34 (d, J=7.2 Hz, 1H), 5.44 (s, 1H), 4.78 (brs, 1H, Exc), 3.41-3.38 (m, 2H), 3.16 (d, J=6.0 Hz, 2H), 2.68 (t, J=6.0 Hz, 2H), 2.59 (t, J=7.6 Hz, 2H), 1.93-1.81 (m, 4H), 1.44 (s, 9H)
LC-MS: m/z=292.3 [M+H]$^+$ at RT 3.41 (97.9% purity)

3-(5,6,7,8-tetrahydro-1,8-naphthyridin-2-yl)propan-1-amine (6b)

To a stirred solution of S-024 (0.25 g, 0.85 mmol, 1.00 equiv.) in DCM (5 mL), cooled to 0° C., TFA (0.13 mL, 1.69 mmol, 2.00 equiv.) was added. The reaction was warmed to RT and stirred for 4 h. After consumption of the starting material (by TLC), the reaction mixture was concentrated under reduced pressure to afford crude compound 6b (0.30 g) as a thick syrup which was used in the next step without purification.

5-bromo-2-(difluoromethoxy) pyridine (2)

To a stirred solution of compound 1 (4.50 g, 25.8 mmol, 1.0 equiv.) in anhydrous MeCN (80 mL), sodium 2-chloro-2,2-difluoroacetate (4.89 g, 31.0 mmol, 1.20 equiv.) was added at RT and stirred at 70° C. for 48 h. After consumption of the starting material (by TLC), the reaction mixture was brought to RT and diluted with NH$_4$Cl solution (30 mL). The aqueous layer was extracted with EtOAc (2×40 mL). The combined organic layers were washed with brine solution (2×50 mL), dried over anhydrous Na$_2$SO$_4$, filtered and concentrated under reduced pressure to give the crude compound which was purified by column chromatography (2% EtOAc/hexane) to afford compound 2 (3.2 g, 57%) as pale yellow syrup.
TLC: 5% EtOAc/Hexane (R$_f$: 0.5) z
$^1$H NMR (400 MHz, CDCl$_3$): δ 8.25 (d, J=2.8 Hz, 1H), 7.82 (dd, J=2.4, 6.4 Hz, 1H), 7.40 (t, J=72.8 Hz, 1H), 6.83 (d, J=8.8 Hz, 1H)
LC-MS: m/z=224.7 [M+H]$^+$ at RT 4.22 (98.2% purity)

(E)-tert-butyl 3-(6-(difluoromethoxy)pyridin-3-yl)acrylate (3)

To a stirred solution of tert-butyl acrylate (9.99 g, 78.1 mmol, 3.50 equiv.), Et$_3$N (8.5 mL, 60.2 mmol, 2.70 equiv.), N-methyl pyrrolidine (20 mL), Tritolylphosphine (1.17 g, 3.52 mmol, 0.16 equiv.) followed by Pd(OAc)$_2$ (0.50 g, 2.22 mmol, 0.09 equiv.) were added. The temperature was gradually raised to 90° C. and compound 2 (5.00 g, 22.3 mmol, 1.0 equiv.) in NMP (10 mL) was added drop wise and stirred at 90° C. for 12 h. After consumption of the starting material (by TLC), the reaction mixture was filtered through pad of celite and washed with EtOAc (50 mL). The combined filtrate was washed with cold water (2×50 mL) followed by NaOCl (50 mL), brine solution (50 mL). The organic layer was dried over anhydrous Na$_2$SO$_4$, filtered and concentrated under reduced pressure to give the crude residue which was purified by column chromatography (3% EtOAc/hexane) to afford compound 3 (4.0 g, 66%) as yellow solid.
TLC: 5% EtOAc/Hexane (R$_f$: 0.5)
$^1$H NMR (400 MHz, CDCl$_3$): δ 8.28 (d, J=2.4 Hz, 1H), 7.88 (dd, J=2.0, 6.4 Hz, 1H), 7.56 (d, J=16.0 Hz, 1H), 7.55 (t, J=45.6 Hz, 1H), 6.91 (d, J=8.4 Hz, 1H), 6.34 (d, J=16.0 Hz, 1H), 1.53 (s, 9H)
LC-MS: m/z=272 [M+H]$^+$ at RT 4.16 (99.5% purity)

(S)-tert-butyl 3-(benzyl((R)-1-phenylethyl)amino)-3-(6-methoxypyridin-3-yl)propanoate (5)

To a stirred solution of compound 4 (0.39 g, 1.85 mmol, 2.0 equiv.) in THF (5 mL), cooled to −30° C., n-BuLi (0.66 mL, 1.65 mmol, 1.79 equiv.) was added and then cooled to −78° C. Compound 3 (0.25 g, 0.92 mmol, 1.0 equiv.) dissolved in THF (3 mL) was added to the reaction mixture, stirred for 30 min and quenched with saturated ammonium chloride. The reaction mixture was extracted with EtOAc (2×20 mL). The combined organic extracts were washed with 10% AcOH, brine solution which was dried over anhydrous Na$_2$SO$_4$, filtered and concentrated under reduced pressure to give the crude compound (mixture of 3 and 5, 0.17 g) as thick syrup, which was directly used in the next step.
TLC: 5% EtOAc/Hexane (R$_f$: 0.5)
LC-MS: m/z=483 [M+H]$^+$ at RT 4.66 (75.1% purity)

Synthesis of (S)-tert-butyl 3-amino-3-(6-(difluoromethoxy)pyridin-3-yl)propanoate (S-029)

To a stirred solution of compound 5 (0.80 g, crude mixture) in EtOAc (5 mL) and AcOH (0.5 mL), 20% Pd(OH)$_2$ (50 mg) was added under N$_2$ atmosphere. The reaction mixture was stirred under H$_2$ atmosphere (40 psi) at RT for 2 h. After consumption of the starting material (monitored by TLC), the reaction mixture was filtered through a pad of celite. Filtrate was concentrated under reduced pressure to afford crude compound which was purified by column chromatography (2% MeOH/DCM) to furnish S-029 (0.3 g, 63%) as yellow syrup.
TLC: 5% MeOH/DCM (R$_f$: 0.3)
$^1$H NMR (400 MHz, CDCl$_3$): δ 8.17 (d, J=2.8 Hz, 1H), 7.78 (dd, J=2.4, 6.4 Hz, 1H), 7.44 (t, 73.2 Hz, 1H), 6.88 (d, J=8.4 Hz, 1H), 4.43-4.40 (m, 1H), 2.65-2.56 (m, 2H), 1.42 (s, 9H)
LC-MS: m/z=274 [M+H]$^+$ at RT 2.76 (99.8% purity)

(S,E)-tert-Butyl 3-(6-(tert-butoxy)pyridin-3-yl)-3-((2,2-dimethoxyethylidene)amino)propanoate (7)

To a stirred solution of dimethoxy acetaldehyde (0.44 mL, 2.50 mmol, 1.20 equiv., 60% in water) in DCM (10 mL), cooled to 0° C., anhydrous MgSO$_4$ (10 g) was added followed by S-029 (600 mg, 2.08 mmol, 1.0 equiv.) in DCM (5 mL). The reaction was continued at RT for 2 h and filtered through a pad of celite, the filtrate was concentrated under reduced pressure to afford compound 7 (650 mg, crude) as a yellow liquid which was used in the next step without any purification.
TLC: 5% MeOH/DCM (R$_f$: 0.5)

(S)-tert-butyl 3-(6-(difluoromethoxy)pyridin-3-yl)-3-((2,2-dimethoxyethyl)amino)propanoate (8)

To a stirred solution of compound 7 (0.65 g, crude, 1.0 equiv.) in MeOH (7 mL), cooled to 0° C., NaBH(CN)$_3$ (0.13 g, 2.09 mmol, 1.20 equiv.) was added and the reaction mixture was stirred at RT for 2 h. After consumption of the starting material (by TLC), MeOH was removed under reduced pressure to give the crude residue which was diluted with water (10 mL) and extracted with EtOAc (2×10 ml). The combined organic extracts were dried over anhydrous Na$_2$SO$_4$, filtered and concentrated under reduced pressure to give the crude material which was purified by column chromatography (2% MeOH/DCM) to afford compound 8 (0.52 g, 79%) as a thick syrup.
TLC: 5% MeOH/DCM (R$_f$: 0.7)
$^1$H NMR (400 MHz, CDCl$_3$): δ 8.13 (d, J=2.0 Hz, 1H), 7.75 (dd, J=2.4, 6.0 Hz, 1H), 7.44 (t, J=73.2 Hz, 1H), 6.87 (d, J=8.4 Hz, 1H), 4.43-4.37 (m, 2H), 4.06-4.02 (m, 1H), 3.60-3.54 (m, 2H), 3.35 (s, 3H) 3.31 (s, 3H), 2.66-2.57 (m, 2H), 1.39 (s, 9H)

LC-MS: m/z=377 [M+H]$^+$ at RT 2.96 (92.3% purity)

(S)-tert-butyl 3-(6-(difluoromethoxy)pyridin-3-yl)-3-(1-(2,2-dimethoxyethyl)-3-(3-(5,6,7,8-tetrahydro-1,8-naphthyridin-2-yl)propyl)ureido)propanoate (10)

To a stirred solution of compound 8 (375 mg, 0.99 mmol, 1.0 equiv.) in dry DCM (5 mL), cooled to 0° C., triphosgene (1.50 mL, 2.99 mmol, 3.00 equiv., 20% in PhMe) followed by Et$_3$N (0.30 mL, 2.09 mmol, 2.10 equiv) were added. The reaction mixture was slowly brought to RT and stirred for 2 h. After completion of the starting material, volatiles were evaporated to afford the crude compound 9, which was used directly in the next step without purification. A solution of compound 9 in DCE (2 mL) was added to a solution of compound 6b (400 mg, 1.32 mmol, 1.32 equiv.) in DCM (5 mL), Et$_3$N (0.55 mL, 3.98 mmol, 4.00 equiv) at 0° C. and stirred at RT for 4 h. After consumption of the starting material (monitored by TLC), the reaction mixture was concentrated under reduced pressure to give the crude residue which was purified by column chromatography (2% MeOH/DCM) to afford compound 10 (0.40 g, 67%) as a thick syrup.

TLC: 5% MeOH/DCM (R$_f$: 0.2)

$^1$H NMR (400 MHz, CDCl$_3$): δ 8.13 (d, J=2.8 Hz, 1H), 7.79 (dd, J=2.4, 6.4 Hz, 1H), 7.62 (tt, J=72.8 Hz, 1H), 7.12 (d, J=6.4 Hz, 1H), 6.86 (d, J=8.4 Hz, 1H), 6.36 (d, J=3.6 Hz, 1H), 6.22 (t, J=4.8 Hz, 1H), 5.75 (t, J=7.6 Hz, 1H), 4.26 (t, J=5.2 Hz, 1H), 3.45-3.38 (m, 8H), 3.27-3.13 (m, 3H), 2.99-2.93 (m, 2H), 2.71-2.59 (m, 5H), 1.93-1.83 (m, 5H), 1.39 (s, 9H)

LC-MS: m/z=594 [M+H]$^+$ at RT 3.42 (88.1% purity)

(S)-tert-Butyl 3-(6-(difluoromethoxy)pyridin-3-yl)-3-(2-oxo-3-(3-(5,6,7,8-tetrahydro-1,8-naphthyridin-2-yl)propyl)-2,3-dihydro-1H-imidazol-1-yl)propanoate (11)

To a stirred solution of compound 10 (0.20 g, 0.34 mmol, 1.0 equiv.) in THF (4 mL), at −10° C., 1 M sulphuric acid (0.8 mL) was added. The reaction was slowly warmed to RT and stirred for 10 h. After consumption of the starting material (monitored by LCMS), THF was removed and the crude residue was neutralized with sodium hydroxide (50 wt %) till pH~7. The aqueous layer was extracted with 5% MeOH/DCM (3×20 mL) and the combined organic extracts were dried over anhydrous Na$_2$SO$_4$, filtered and concentrated under reduced pressure to furnish compound 11 (0.22 g, crude) as a syrup.

TLC: 10% MeOH/DCM (R$_f$: 0.5)

LC-MS: m/z=530 [M+H]$^+$ at RT 4.06 (72.8% purity)

(S)-tert-Butyl 3-(6-(difluoromethoxy)pyridin-3-yl)-3-(2-oxo-3-(3-(5,6,7,8-tetrahydro-1,8-naphthyridin-2-yl)propyl)imidazolidin-1-yl)propanoate (12)

To a stirred solution of compound 11 (0.45 g, crude, 1.0 equiv.) in EtOH (8 mL), 20% Pd/C (200 mg) was added under N$_2$ atmosphere. The reaction mixture was stirred under H$_2$ atmosphere (40 psi) at RT for 36 h. After consumption of the starting material the reaction mixture was filtered through a pad of celite, the filtrate was concentrated under reduced pressure to afford crude compound 12, which was purified by chiral preparative HPLC to afford compound 12 (450 mg, crude) as an off-white solid.

TLC: 10% MeOH/DCM (R$_f$: 0.5)

LC-MS: m/z=532.6 [M+H]$^+$ at RT 3.99 (80.1% purity)

(S)-3-(6-(difluoromethoxy)pyridin-3-yl)-3-(2-oxo-3-(3-(5,6,7,8-tetrahydro-1,8-naphthyridin-2-yl)propyl)imidazolidin-1-yl)propanoic acid (Compound A1 in Table 1)

To a stirred solution of compound 12 (0.40 g, crude, 1.0 equiv.) in DCM (2 mL), cooled to −10° C., TFA (0.5 mL) was added under N$_2$ atmosphere. The reaction was slowly brought to RT and stirred for 2 h; after consumption of the starting material, volatiles were evaporated to afford crude (400 mg) compound, which was purified by chiral preparative HPLC to afford compound A1 as an off-white solid.

TLC: 10% MeOH/DCM (R$_f$: 0.3)

$^1$H NMR (400 MHz, CD$_3$OD): δ 8.20 (d, J=2.4 Hz, 1H), 7.85 (dd, J=2.4, 6.4 Hz, 1H), 7.53 (t, J=2.4 Hz, 1H), 7.50 (d, J=7.2 Hz, 1H), 6.98 (d, J=8.4 Hz, 1H), 6.57 (d, J=7.2 Hz, 1H), 5.51 (dd, J=3.6, 8.0 Hz, 1H), 3.68-3.61 (m, 1H), 3.52-3.46 (m, 3H), 3.38 (m, 1H), 3.24-3.17 (m, 1H), 3.07-2.98 (m, 2H), 2.90-2.62 (m, 6H), 2.09-1.81 (m, 4H).

LC-MS: m/z=476 [M+H]$^+$ at RT 2.78 (97.9% purity)

HPLC purity: 96.4%; Chiral Purity: 99%

Example 2

Synthesis of (S)-3-(6-(difluoromethoxy)pyridin-3-yl)-3-(2-oxo-3-((3-((5,6,7,8-tetrahydro-1,8-naphthyridin-2-yl)methyl)oxetan-3-yl)methyl)imidazolidin-1-yl)propanoic acid (Compound A2 in Table 1)

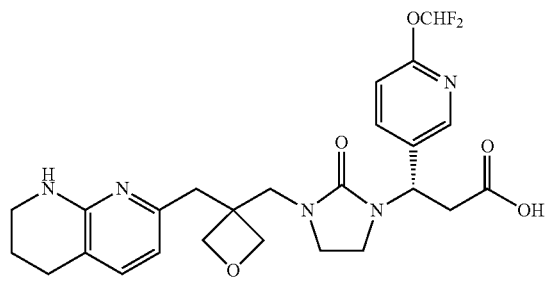

The synthetic route is the same as Example 1 except for substituting at Step-8: (3-((5,6,7,8-tetrahydro-1,8-naphthyridin-2-yl)methyl)oxetan-3-yl)methanamine

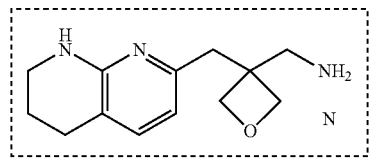

for compound 6b and continuing the synthetic scheme using the same reaction conditions.

Example 3

Synthesis of (S)-3-(3-(2,2-difluoro-3-(5,6,7,8-tetrahydro-1,8-naphthyridin-2-yl)propyl)-2-oxoimidazolidin-1-yl)-3-(6-(difluoromethoxy)pyridin-3-yl)propanoic acid (Compound A3 in Table 1)

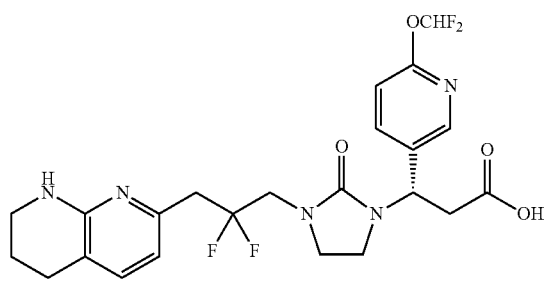 [SMILES: O=C(O)C[C@@H](c1ccc(OC(F)F)nc1)N1CCN(CC(F)(F)Cc2ccc3c(n2)NCCC3)C1=O]

The synthetic route is the same as Example 1 except for substituting at Step-8: 2,2-difluoro-3-(5,6,7,8-tetrahydro-1,8-naphthyridin-2-yl)propan-1-amine

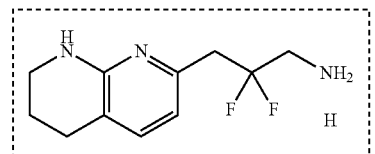

for compound 6b and continuing the synthetic scheme using the same reaction conditions.

Example 4

Synthesis of (S)-3-(3-(2,2-difluoro-3-(5,6,7,8-tetrahydro-1,8-naphthyridin-2-yl)propyl)-2-oxoimidazolidin-1-yl)-3-(6-methoxypyridin-3-yl)propanoic acid (Compound A4 in Table 1)

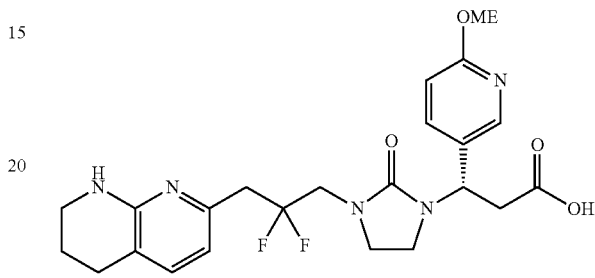

The synthetic scheme is the same as Example 3, except the synthesis in Step 1 uses sodium 2-chloroacetate instead of sodium 2-chloro-2,2-difluoroacetate. The synthesis proceeds under the same conditions as Example 3.

The synthesis of the Gem-Difluoride fragment H, shown in the dashed boxes, is shown in Schemes 2-4:

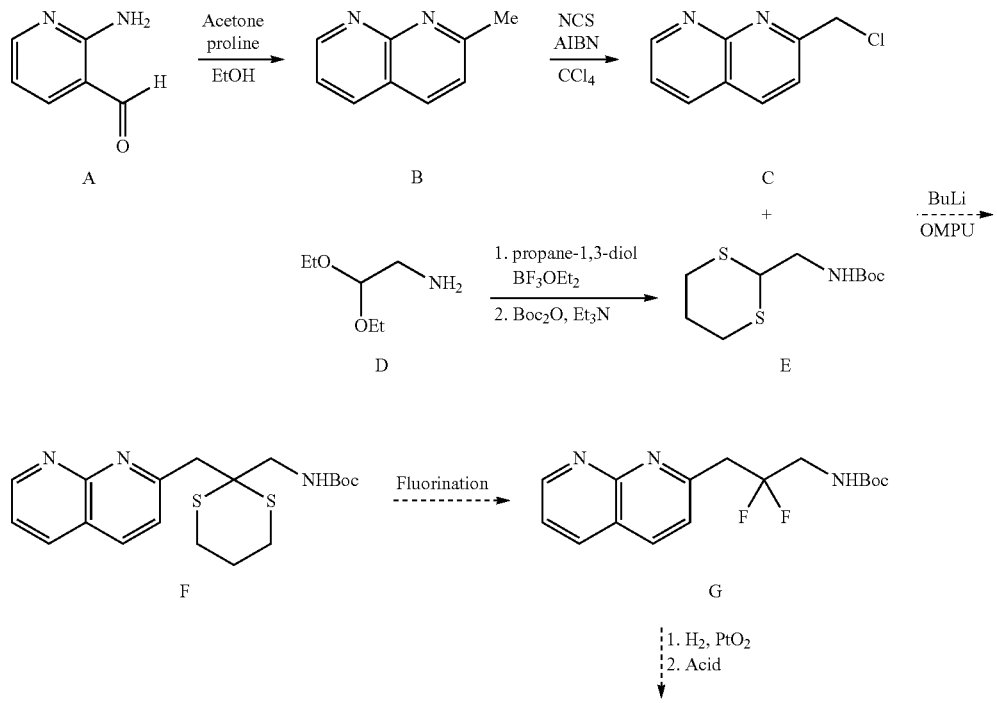

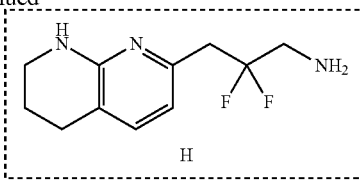

The preparation of intermediates C and E is detailed in the literature and is depicted above (for C; Campbell, J. E.; Hewitt, M. C.; Jones, P.; Xie, L. WO2011150156 and for E; Seebach, D.; Maestro, M. A.; Sefkow, M.; Adam, G.; Hintermann, S.; Neidlein, A. *Liebigs Ann. Chem.*, 1994, 701-717). The formation of the dianion of E has been described, and it was used to displace substituted benzylic chlorides (Bradshaw, B.; Evans, P.; Fletcher, J.; Lee, A. T. L.; Mwashimba, P. G.; Oehlrich, D.; Thomas, E. J.; Davies, R. H.; Allen, B. C. P.; Broadley, K. J.; Hamrouni, A.; Ascargueil, C. *Org. Biomol. Chem.*, 2008, 6, 2138-2157.); this event similarly affords complex dithiane F. Fluorodesulfurization of thioketals has been described with several reagents (Sondej, S. C.; Katzenellenbogen, J. A. *J. Org. Chem.*, 1986, 51, 3508-13.); intermediate G is reduced and deprotected as described in the literature (Wang, J. US20040038963). Fragment H is inserted into the known route to produce the target compounds.

Scheme 3:
Route 2:

Known β-ketoester P is cyclized, then ketalized with 1,2-dithiol to form lactam Q. Ring opening with a phosphonate enolate affords Horner-Emmons reagent R, which is immediately followed by a Friedlander reaction to intersect scheme 2, route 1 at intermediate F (Yasuda, N.; Hsiao, Y.; Jensen, M. S.; Rivera, N. R.; Yang, C.; Wells, K. N.; Yau, J.; Palucki, M.; Tan, L.; Dormer, P. G.; Volante, R. P.; Hughes, D. L.; Reider, P. J. *J. Org. Chem.*, 2004, 69, 1959-1966).

Scheme 4:
Route 3:

Reformatsky reaction of known 1,8-naphthyridine S affords carbinol T (Linderman, R. J.; Graves, D. M. *J. Org. Chem.*, 1989, 54, 668). Barton deoxygenation utilizing conditions reported for very similar substrates affords U (Hallinanm, E. A.; Hagan, T. J.; Husa, R. K.; Ysymbalov, S.; Rao, S. N.; vanHoeck, J.-P.; Rafferty, M. F.; Stapelfeld, A.; Savage, M. A.; Reichman, M. *J. Med. Chem.* 1993, 36, 3298-3299). Reduction of the ester followed by triflation and displacement affords azide V. Selective reduction affords the requisite amine H (Wang, J. US20040038963).

The synthesis of the Oxetane fragment N, shown in the dashed boxes, is shown in Schemes 5-7:

Scheme 5:

Route 1:

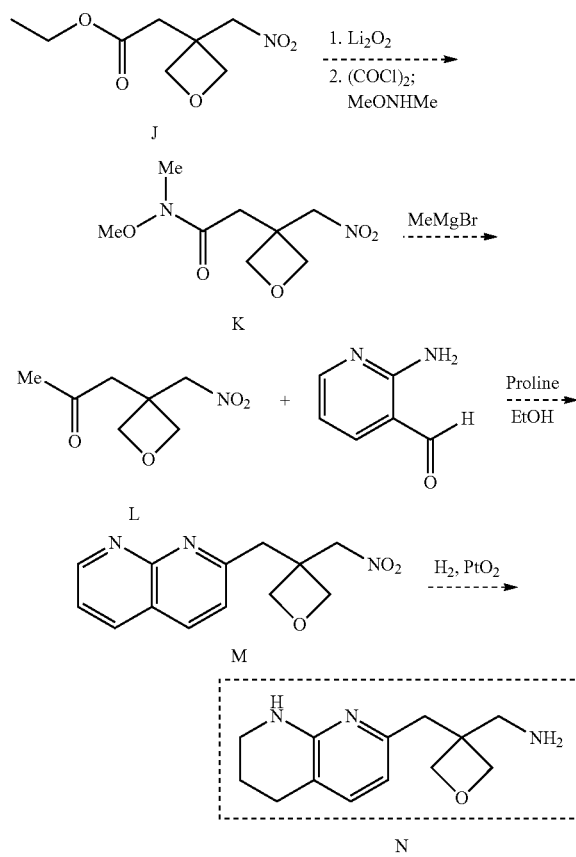

Commercially available ester J is transformed to the Weinreb amide K, then treated with methyl Grignard to form ketone L (Nahm, S.; Weinreb, S. M. *Tetrahedron Lett.* 1981, 22, 3815). A Friedlander condensation with 2-aminonicotinaldehyde affords 1,8-napthyridine M (Friedlander, P. *Ber. Dtsch. Chem. Ges.* 1882, 15, 2572). A well-precedented reduction affords the requisite tetrahydro-fragment N (Wang, J. US20040038963).

Scheme 6:

Route 2:

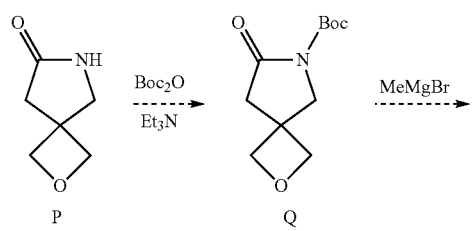

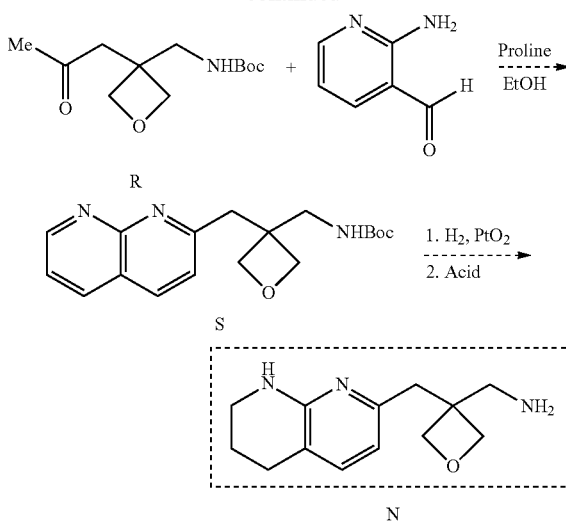

Commercially available lactam P is protected as a Boc-carbonate and opened with a Grignard reagent to form ketone R. A similar Friedlander/reduction/deprotection sequence affords fragment N.

Scheme 7:

Route 3:

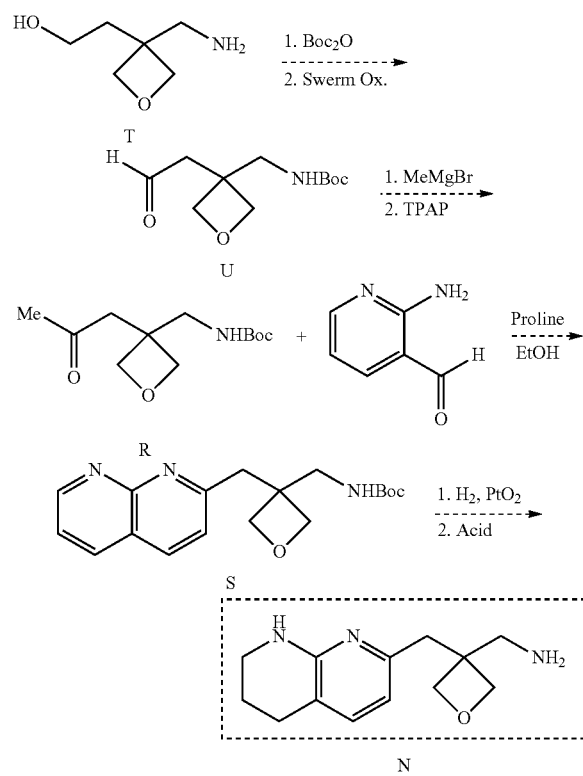

Aminoalcohol T is protected as a carbonate and oxidized. The intermediary aldehyde U is treated with a methyl Grignard reagent and oxidized to the ketone R. A similar Friedlander/reduction/deprotection sequence affords requisite fragment N.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

What is claimed:

1. A compound of formula I:

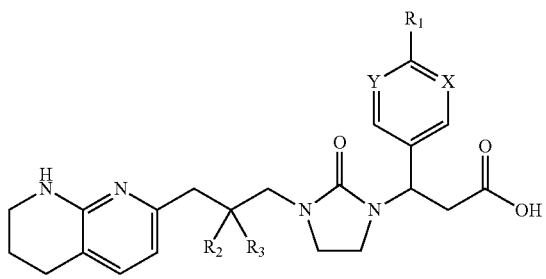

(I)

or a pharmaceutically acceptable salt or solvate thereof, wherein
X is selected from CH and N;
Y is selected from CH and N;
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula I contains at least one fluorine atom.

2. A compound of formula II:

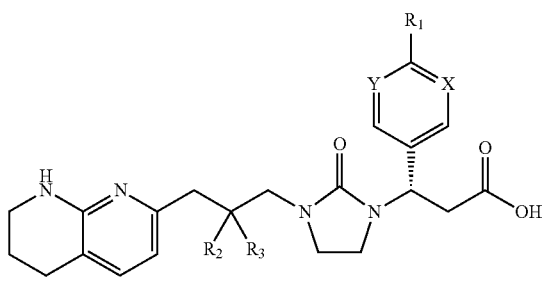

(II)

or a pharmaceutically acceptable salt or solvate thereof, wherein
X is selected from CH and N;
Y is selected from CH and N;
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula II contains at least one fluorine atom.

3. A compound of formula III:

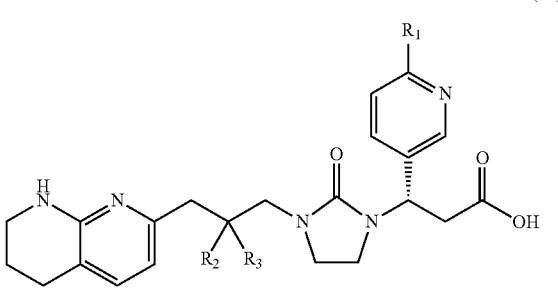

(III)

or a pharmaceutically acceptable salt or solvate thereof, wherein
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula III contains at least one fluorine atom.

4. A compound of formula IV:

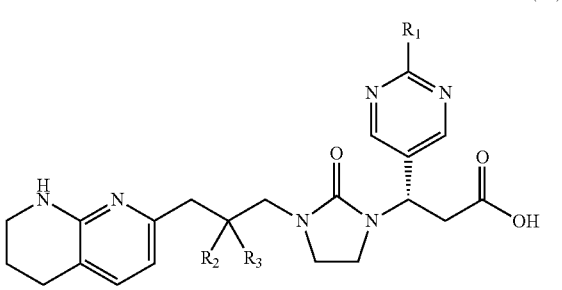

(IV)

or a pharmaceutically acceptable salt or solvate thereof, wherein
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F,
or $R_2$ and $R_3$ taken together with the carbon atom to which they are attached form a 3- or 4-membered carbocyclic or heterocyclic ring,
provided that the compound of formula IV contains at least one fluorine atom.

5. A compound of formula V:

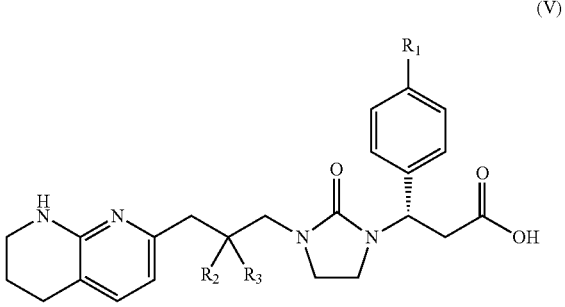

(V)

or a pharmaceutically acceptable salt or solvate thereof, wherein
$R_1$ is $C_1$-$C_6$ alkoxy wherein said $C_1$-$C_6$ alkoxy is substituted with 0, 1, 2, 3, 4, or 5 fluorine atoms; and
$R_2$ and $R_3$ are each independently selected from H and F, or R₂ and R₃ taken together with the carbon atom to which they are attached form a 3- or 4-membered carbocyclic or heterocyclic ring, provided that the compound of formula V contains at least one fluorine atom.

6. A pharmaceutical composition comprising a compound of claim 1 or a pharmaceutically acceptable salt or solvate thereof and a pharmaceutical carrier, diluent, or excipient.

7. A pharmaceutical composition comprising a compound of claim 2 or a pharmaceutically acceptable salt or solvate thereof and a pharmaceutical carrier, diluent, or excipient.

8. A pharmaceutical composition comprising a compound of claim 3 or a pharmaceutically acceptable salt or solvate and a pharmaceutical carrier, diluent, or excipient.

9. A pharmaceutical composition comprising a compound of claim 4 or a pharmaceutically acceptable salt or solvate thereof and a pharmaceutical carrier, diluent, or excipient.

10. A pharmaceutical composition comprising a compound of claim 5 or a pharmaceutically acceptable salt or solvate thereof and a pharmaceutical carrier, diluent, or excipient.

11. The compound of claim 1, selected from the group consisting of:

or a pharmaceutically acceptable salt or solvate thereof.

12. A pharmaceutical composition comprising a compound of claim 11 or a pharmaceutically acceptable salt or solvate thereof and a pharmaceutical carrier, diluent, or excipient.

13. The compound of claim 1, selected from the group consisting of:

or a pharmaceutically acceptable salt or solvate thereof.

14. A pharmaceutical composition comprising a compound of claim 13 or a pharmaceutically acceptable salt or solvate thereof and a pharmaceutical carrier, diluent, or excipient.

* * * * *